(12) United States Patent
Wu et al.

(10) Patent No.: US 12,349,665 B2
(45) Date of Patent: Jul. 8, 2025

(54) ANIMAL MODEL FOR HEPATOCELLULAR CARCINOMA AND USES THEREOF

(71) Applicants: TAIPEI VETERANS GENERAL HOSPITAL, Taipei (TW); NATIONAL YANG-MING UNIVERSITY, Taipei (TW)

(72) Inventors: Jaw-Ching Wu, Taipei (TW); Yu-Wei Chiou, Taipei (TW)

(73) Assignees: TAIPEI VETERANS GENERAL HOSPITAL, Taipei (TW); NATIONAL YANG-MING UNIVERSITY, Taipei (TW)

( * ) Notice: Subject to any disclaimer, the term of this patent is extended or adjusted under 35 U.S.C. 154(b) by 1208 days.

(21) Appl. No.: 17/127,496

(22) Filed: Dec. 18, 2020

(65) Prior Publication Data
US 2021/0185991 A1    Jun. 24, 2021

Related U.S. Application Data

(60) Provisional application No. 62/949,658, filed on Dec. 18, 2019.

(51) Int. Cl.
*A01K 67/0276* (2024.01)
*A61K 49/00* (2006.01)
(Continued)

(52) U.S. Cl.
CPC ...... *A01K 67/0276* (2013.01); *A61K 49/0008* (2013.01); *C12N 7/00* (2013.01);
(Continued)

(58) Field of Classification Search
CPC .......... A01K 67/0276; A01K 2217/058; A01K 2227/105; A01K 2267/0331; A01K 2217/052; A01K 2217/075; A01K 2217/15; A01K 67/0275; A61K 49/0008; A61K 31/713; C12N 7/00; C12N 15/86; C12N 2730/10043; C12N 15/113; C12N 2310/141; C12N 2730/10122; C07K 14/005
See application file for complete search history.

(56) References Cited

PUBLICATIONS

Teng (Teng, Yuan-Chi et al. "Hepatocellular carcinoma mouse models: Hepatitis B virus-associated hepatocarcinogenesis and haploinsufficient tumor suppressor genes." World journal of gastroenterology vol. 22,1 (2016): 300-25.) (Year: 2016).*

(Continued)

*Primary Examiner* — Jeremy C Flinders
*Assistant Examiner* — Thomas R. Amick
(74) *Attorney, Agent, or Firm* — Birch, Stewart, Kolasch & Birch, LLP

(57) ABSTRACT

The invention provides an animal model for hepatocellular carcinoma and uses thereof. The genome of the animal model includes a hepatitis B virus genome and a single set of endogenous miR-122 that is partially deleted. Due to the early and high incidence of spontaneous hepatocellular carcinoma in the animal model and its abnormal fat metabolism, the animal model can be used to screen candidate agents for prevention or treatment of hepatitis B virus and hepatocellular carcinoma or other diseases or to develop uses for diagnosis and prediction of hepatocellular carcinoma.

10 Claims, 19 Drawing Sheets
(13 of 19 Drawing Sheet(s) Filed in Color)
Specification includes a Sequence Listing.

(51) Int. Cl.
*C12N 7/00* (2006.01)
*C12N 15/86* (2006.01)

(52) U.S. Cl.
CPC ........ *C12N 15/86* (2013.01); *A01K 2217/058* (2013.01); *A01K 2227/105* (2013.01); *A01K 2267/0331* (2013.01); *C12N 2730/10043* (2013.01)

(56) References Cited

PUBLICATIONS

Bonvicino, Cibele R et al. "Hepatitis B virus lineages in mammalian hosts: potential for bidirectional cross-species transmission." World journal of gastroenterology vol. 20,24 (2014): 7665-74. doi: 10.3748/wjg.v20.124.7665 (Year: 2014).*

* cited by examiner

ANIMAL MODEL FOR HEPATOCELLULAR CARCINOMA AND USES THEREOF

CROSS REFERENCE TO RELATED APPLICATION

This non-provisional application claims the benefit under 35 U.S.C. § 119 (e) to U.S. Provisional Application No. 62/949,658, filed on Dec. 18, 2019, which is hereby expressly incorporated by reference into the present application.

BACKGROUND OF THE INVENTION

Field of the Invention

The invention relates to an animal model for hepatocellular carcinoma, particularly to an animal model for hepatocellular carcinoma caused by hepatitis B.

Description of the Prior Art

Hepatocellular carcinoma is the second most common cancer in Taiwan, with more than 7,000 people dying from it each year. Hepatocellular carcinoma has the third highest mortality rate from cancer in the world, with more than 500,000 patients dying from it each year. Hepatitis B virus (HBV) is the main cause of hepatocellular carcinoma, and chronic hepatitis may lead to cirrhosis or hepatocellular carcinoma.

Current research on HBV lacks an appropriate animal model. Although chimpanzees can be infected with hepatitis B virus, they are legally protected and too expensive to be widely used. Although marmots and Peking ducks can be infected with woodchuck hepatitis virus (WHV) and duck hepatitis B virus (DHBV), which are similar to hepatitis B virus, these two animals are not ideal animal model for hepatitis B virus infection and hepatocellular carcinoma research due to the differences of characteristics and disease process between human HBV and the two viruses, the difficulties of reproduction and care of the two animals, and high costs.

At present, except chimpanzees, the animal model closest to a real human body is human liver transplanted mice. However, it requires high skill to produce such an animal model, and the transplanted mice is too weak to take care of. Only specialized personnel in specific large laboratories can produce such an animal model, and the number is too few to promote. The animal model is expensive and difficult to reproduce in large numbers for general hepatitis and hepatocellular carcinoma research. Furthermore, such mice are often used for short-term viral infection studies or antiviral drug evaluation, and rarely for studies of hepatocellular carcinoma. Moreover, human liver is scarce and expensive. Due to the different effects of transplantation in each mouse, individual variation is large. HBV transgenic mice can express HBV in large quantities, and they can be used as a platform for antiviral drug testing. Although some mouse strains with high viral load may develop hepatocellular carcinoma, general hepatitis B virus transgenic mice have a low carcinogenicity, unless a chemical carcinogen is added. However, the mechanisms of carcinogenesis between addition of carcinogen and infection of human hepatitis B virus are different, and therefore, general hepatitis B virus transgenic mice treated with a chemical carcinogen cannot be used for clinical and transcription research.

miR-122 is a tumor suppressor gene, which is mainly present in liver. During infection of human hepatitis B virus, as the infection time increases, the level of miR-122 gradually decreases. miR-122 is closely related to the occurrence of hepatocellular carcinoma, and as liver tumor progresses (Tsai WC et al. Hepatology 2009, 565 citations) [1], miR-122 is further reduced, which also affects the progression of hepatocellular carcinoma. Previous studies showed that all of the miR-122 knock-out mice developed hepatocellular carcinoma (Tsai W C et al. MicroRNA-122. J Clin Invest 2012; 122 (8): 2884-2897. With an editorial and 583 citations) [2]. However, miR-122 reduces, rather than being double knocked out, in humans with hepatocellular carcinoma. Therefore, the mechanisms of carcinogenesis between the miR-122 knock-out mice and humans with hepatocellular carcinoma are different. There is an urgent need to establish an animal model that more closely resembles carcinogenesis of hepatocytes from hepatitis B in humans.

Changes in human liver mitochondrial function and miR-122 down-regulation can affect fat metabolism and cause fatty liver. Non-alcoholic fatty liver may also cause hepatocellular carcinoma, which is an important problem affecting global human health. Chronic hepatitis B virus infection with fatty liver and metabolic syndrome significantly increases the chance of cirrhosis and hepatocellular carcinoma. At present, there is no animal model for simultaneously studying changes of liver mitochondrial function, and how the relationship between miR-122 down-regulation and chronic hepatitis B increases hepatocellular carcinoma.

SUMMARY OF THE INVENTION

In view of lack of an ideal animal model of hepatocellular carcinoma caused by hepatitis B in the prior art, the present invention provides a method for producing a non-human transgenic animal model for hepatocellular carcinoma.

In one aspect, the present invention provides a method for producing a non-human transgenic animal model for hepatocellular carcinoma, comprising: a) providing a polynucleotide expression vector encoding a hepatitis B virus (HBV) genome comprising enhancer I/II, open reading frames X, C, PS, and S at the 5' end and a polyadenylation site at the 3' end; b) introducing the polynucleotide expression vector into a genetic locus of an animal which is the same species as a non-human transgenic animal to produce a non-human transgenic animal containing a gene encoding the HBV genome; c) providing an endogenous miR-122 knock-out animal, which is the same species as the non-human transgenic animal of step b); and d) hybridizing the non-human transgenic animal containing the gene encoding the HBV genome and the endogenous miR-122 knock-out animal to produce a non-human transgenic animal having a genome encoding the HBV genome and the endogenous miR-122 knock-out. Genetic recombination technology was used to establish liver-specific HBV transgenic genes.

In one embodiment of the present invention, the non-human transgenic animal is a rodent, preferably a mouse or a rat.

In one embodiment of the present invention, the HBV genome includes genotype A, wild-type genotype B, genotype C, genotype D, genotype E, genotype F, genotype G, genotype H, genotype I, and genotype J. Genotype B is a more common genotype in East Asia as well as the main genotype distributed in Taiwan. In another embodiment, it includes BCP mutation, which is carcinogenic, wild type having mutations on reverse transcriptase activation genes that are common in drug resistance virus, and drug-resistant HBV genome. Wild-type mice can be used to screen for the efficacy of novel antiviral drugs. Drug-resistant mice can be used to screen for novel drugs that may cause receivers to develop resistance, and therefore such drugs can be eliminated at early stage of drug development. Combining the two animal models can quickly screen for novel drugs with high efficiency of eliminating virus and low chance to develop resistance. The animal model is prone to carcinogenesis, which can be used as an animal model for hepatocellular carcinoma, as a platform for screening for anticancer drugs, and as an animal model for cancer research.

According to the present invention, the drug resistant HBV genome is resistant to an antiviral nucleoside analogue, such as adefovir or lamivudine. Results of drug experiment of animal models of the present invention show that the amount of serum virus in mice with wild-type HBV genome decreased by more than a thousand times after the mice were treated with antiviral drugs such as adefovir or lamivudine, whereas the amount of serum virus in mice with the drug resistant HBV genome decreased much less after the mice were treated with antiviral drugs. The amount of virus reduced in the mice with the drug resistant HBV genome is significantly less than the amount of virus reduced in the mice with wild-type HBV genome, indicating the mice with the drug resistant HBV genome have drug resistance.

In one embodiment of the present invention, the drug-resistant HBV genome has at least one amino acid mutation, wherein the amino acid mutation is selected from the group consisting of rtA181V, rtN236T, rtL180M, rtM204V and a combination thereof in a reverse transcriptase region of the HBV genome, in which the numbers represent sites of the amino acid mutation, and the subsequent English letters are amino acids of the mutation. The amino acid mutation is selected from the group consisting of rtL180M, rtM204V, and a combination thereof.

In one embodiment of the present invention, the endogenous miR-122 is heterozygous knock-out or homozygous knock-out, preferably heterozygous knock-out, which can be used to reduce the expression of miR-122, as in general hepatitis B patients, in which miR-122 expression may be reduced.

In another aspect, the present invention provides a method for screening candidate agents with efficacy for preventing or treating hepatocellular carcinoma or other diseases, comprising: a) providing the non-human transgenic animal model for hepatocellular carcinoma produced by disclosed methods; b) administering a candidate agent to the non-human transgenic animal model; and c) comparing the performance of the non-human transgenic animal model administered with the candidate agent to that of the non-administered non-human transgenic animal model, wherein when the candidate agent alleviates a symptom, the candidate agent is selected as an agent having the effect of preventing or treating hepatocellular carcinoma or other diseases.

In one embodiment of the present invention, the agent is for preventing or treating hepatocellular carcinoma, hepatitis, or fatty liver.

In another aspect, the present invention provides a non-human transgenic animal, which has an early and high incidence of spontaneous hepatocellular carcinoma and abnormal fat metabolism. The animal is characterized by endogenous miR-122 knock-out and is the same animal species as the aforementioned animal. The non-human transgenic animal containing the gene encoding the HBV genome and the endogenous miR-122 knock-out animal were hybridized to produce a non-human transgenic animal having a genome encoding the HBV genome and the endogenous miR-122 knock-out.

Therefore, the non-human transgenic animal can be used as a screening platform for novel antiviral drugs and anti-hepatocellular carcinoma drugs.

The present invention further provides a use of a non-human transgenic animal model for screening a candidate agent for preventing or treating hepatocellular carcinoma or other diseases, comprising: a) an aforementioned non-human transgenic animal model; b) providing a candidate agent to the non-human transgenic animal model; and c) comparing the non-human transgenic animal model provided with the candidate agent to the non-human transgenic animal model without the candidate agent, wherein when the candidate agent alleviates a symptom, the candidate agent is selected as an effective agent for preventing or treating hepatocellular carcinoma or other diseases Since the aforementioned non-human transgenic animal, which has a genome encoding the HBV genome and the endogenous miR-122 knock-out, has an early and high incidence of spontaneous hepatocellular carcinoma and abnormal fat metabolism, the present invention also provides a use of miR-122 for preparing a medicament for preventing or treating hepatocellular carcinoma, wherein the medicament effectively improves endogenous miR-122 of an individual in need.

BRIEF DESCRIPTION OF THE DRAWINGS

The patent or application file contains at least one drawing executed in color. Copies of this patent or patent application publication with color drawing will be provided by the USPTO upon request and payment of the necessary fee.

When read in combination with the drawings, the foregoing summary and the following embodiments of the present invention will be better understood. In the drawings:

FIG. 11A is a partial least squares discriminant analysis plot (PLS-DA score plot) showing that fat-soluble metabolites of hepatocellular carcinoma tissue and non-cancer tissue are clearly grouped. The chemical shift in the region between 5.6-6.8 ppm of FIG. 11B is the olefinic protons (b-carotene, vitamin A, and retinoic acid) of conjugated polyenes. FIG. 11C is a comparison between hepatocellular carcinoma tissue (ML-D14122-LT-182-FC) and non-cancer tissue (D14122-LN-182-FC), in which the content of triglyceride and cholesterol was higher in hepatocellular carcinoma tissues, and the content of polyunsaturated fatty acids was lower in hepatocellular carcinoma tissue, which may be caused by a decrease in de novo synthesis of lipid in hepatocellular carcinoma tissues.

FIG. 12A shows that liver miR-122 expression was lower in hepatocellular carcinoma tissues of HBV transgenic mice (LT, N=11) than in normal liver tissues of B6 mice (Liv, N=11). FIG. 12B reveals that the "case-control study" was used to distinguish hepatocellular carcinoma (43 mice, 25 males and 18 females) from non-cancer (32 mice, 11 males and 21 females) from hybrid mice older than 18 months. Blood samples of the early stage (4-8 months old) of the mice were compared to examine 9 possible miR-122 target genes, and the results indicated that CDC25A was significantly higher in the cancer group than that in the non-cancer group. FIG. 12C shows the comparison of the expression of CDC25A gene in liver tissues, indicating that the expression in hepatocellular carcinoma tissues (LT, from 11 HBV transgenic mice) is higher than that in normal liver tissues (Liv, from 11 B6 mice). FIG. 12D shows the gene expression of CDC25A in human HCC surgical specimens. Gene expression levels were extracted from the public domain of the dataset GSE45267 in the Gene Expression Omnibus (GEO) database, including RNA expression profiles of 48 HCC tissues and 39 non-tumor liver tissues, using Affymetrix Human Genome U133 Plus 2.0 gene expression microarray detection. The data related to the two CDC25A RNA detection probe sets (1555772_a_at and 204695_at) were extracted and displayed as a heat map using the generalized correlation map software. The performance of CDC25A was significantly higher in hepatocellular carcinoma tissues than that in non-cancer tissues (t test * $P<0.05$,  $P<0.01$, * $P<0.001$).

DETAILED DESCRIPTION OF THE EMBODIMENTS

Figure 1:
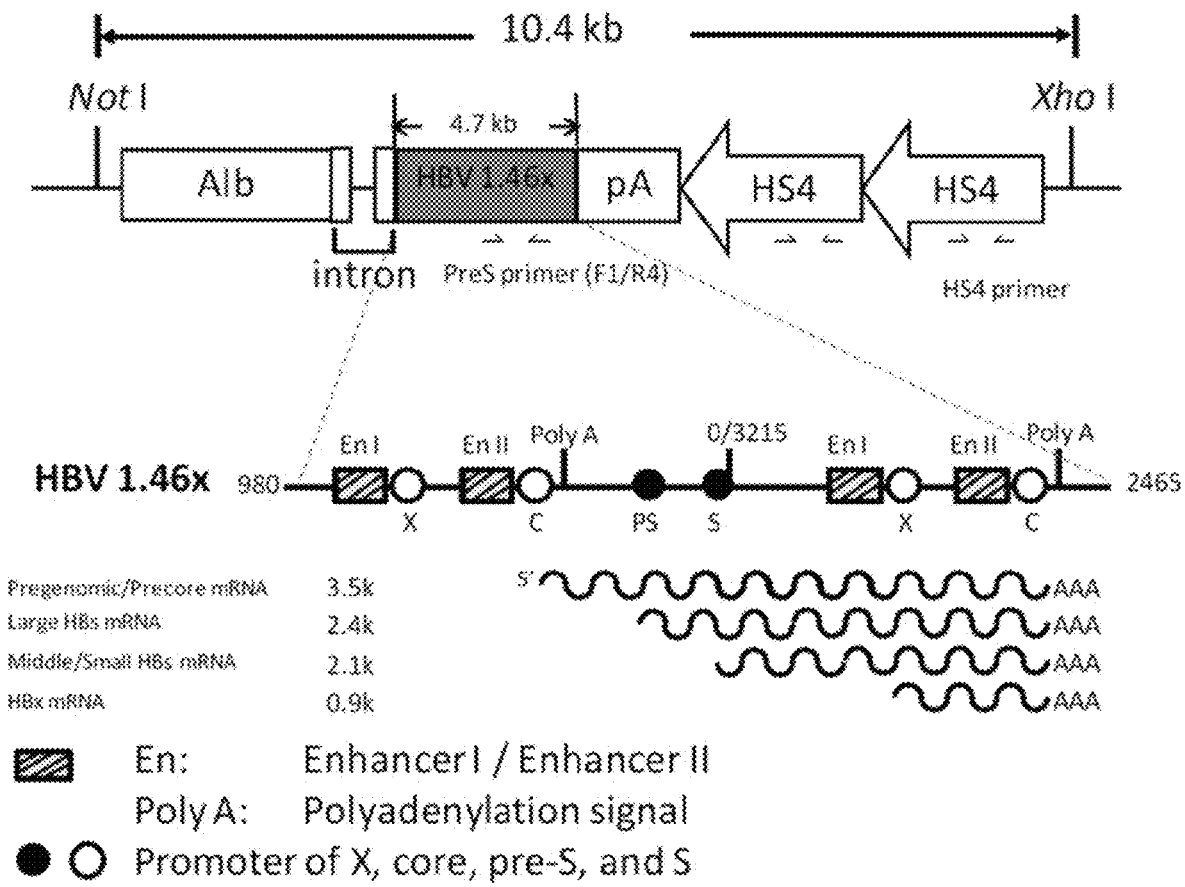
FIG. 1 shows the use of genetic recombination technology to establish liver-specific HBV transgenic genes.
Figure 2:
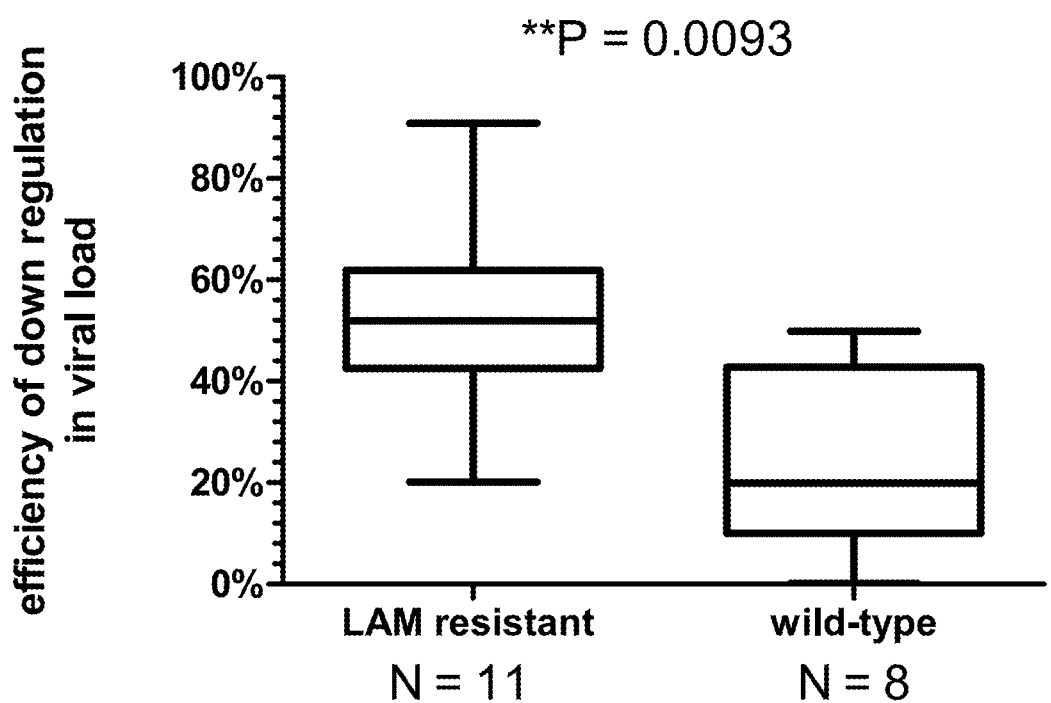
FIG. 2 shows the results of which 3-4 month-old HBV transgenic mouse strains that express lamividine (LAM) resistance (6 mice of strain B00; 5 mice of strain B13) and the HBV transgenic mouse strains that express wild-type hepatitis B virus (3 mice of D11; 5 mice of D14) were orally administrated LAM (feeding concentration of 100 mg/Kg body weight) through a feeding tube, and the amount of virus in serum was measured before feeding and 14 days after feeding. The upper and lower limits of the rectangles in the figure are quartiles, and the horizontal lines within the rectangles indicate the median. Mann-Whitney U test was used for statistical analysis, and p=0.0093, showing the significant differences. Compared with the decrease in the amount of virus after drug administration, the decline in virus in the drug-resistant group was less than that in the wild-type group. The animal model exhibited a similar drug resistance to that of patients with chronic hepatitis B after long-term administration of antiviral drugs such as LAM.

Unless defined otherwise, all technical and scientific terms used herein have the same meaning as commonly understood by one of ordinary skill in the art to which this invention belongs. It should be understood that the terminology used herein is for the purpose of describing embodiments only and is not intended to limit.

As used herein, the singular forms "a," "an," and "the" include plural referents unless the context clearly indicates otherwise. Thus, for example, reference to "a sample" includes a plurality of such samples and equivalents thereof known to those skilled in the art.

As used herein, "gene" refers to any and all isolated coding regions of the genome of a eukaryotic or prokaryotic cell, as well as related non-coding and regulatory regions. The term "gene" also means an open reading frame encoding a specific polypeptide, an intron, and adjacent non-coding nucleotide sequences at the 5' and 3' ends involved in performance regulation. In this regard, a gene may further include control signals, such as promoters, enhancers, termination and/or polyadenylation signals, or heterologous control signals that are naturally associated with a particular gene. The DNA sequence may be cDNA or genomic DNA or a fragment thereof. The gene can be introduced into a suitable vector for extrachromosomal maintenance or integrated into a host.

As used herein, "genetic modification" refers to the use of genetic engineering to add new genetic material to the organism's genome, and the combination of the genome and foreign DNA results in a permanent or temporary genetic change.

As used herein, "non-human transgenic animal" includes any transformable species other than humans, especially non-human mammals, including non-human transgenic animals and their offspring, and cells and tissues obtained from such animals. For example, non-human mammals include primates, ungulates, canines, rodents, or felines. In a specific embodiment, the transgenic animal is a mouse.

As used herein, "microRNA (miRNA)" is an RNA molecule with a length of about 21 to 23 nucleotides that is widely present in eukaryotes and can regulate the expression of other genes. miRNA is transcribed from DNA but cannot be further translated into protein RNA, and thus it is non-coding RNA. miRNA plays an important role in regulating gene expression, cell cycle, and developmental timing of organisms.

Methods for producing transgenic animals are known to those skilled in the art. These methods include embedding, gene knock-out, CRISPR, TALENS, and other similar methods.

In a specific embodiment of the present invention, a non-human transgenic animal expressing hepatitis B virus is provided. The HBV genome encodes enhancer I/II, open reading frames X, C, PS, and S at the 5' end and a polyadenylation site at the 3' end.

In another aspect, the present invention provides a method for producing a non-human transgenic animal model expressing a hepatitis B virus, comprising: a) providing a polynucleotide sequence encoding a hepatitis B virus (HBV) genome comprising enhancer I/II, open reading frames X, C, PS, and S at the 5' end and a polyadenylation site at the 3' end; b) under certain conditions introducing the polynucleotide sequence into an embryonic stem cell of an animal that is the same species as the non-human transgenic animal, the conditions allow the polynucleotide sequence to be homologously recombined into a genetic locus of genome of the embryonic stem cell to produce an embryonic stem cell having polynucleotide encoding HBV genome comprising enhancer I/II, open reading frames X, C, PS, and S at the 5' end and a polyadenylation site at the 3' end; c) injecting the homologously recombined embryonic stem cell into a blastocyst of a non-human transgenic animal; d) introducing the injected blastocyst into a pseudo-pregnant female non-human animal; e) allowing the pseudo-pregnant females animal to give birth to one or more non-human transgenic animals containing a homologous recombinant DNA sequence; and f) backcrossing the primary non-human transgenic animal several generations to produce a stable non-human transgenic animal strain.

In a specific embodiment, the HBV genome comprises genotype A, genotype B, genotype C, genotype D, genotype E, genotype F, genotype G, genotype H, genotype I, and genotype J. Preferably, the HBV genome is genotype B.

In another specific embodiment, the HBV genome is isolated from a blood sample of a chronic hepatitis B patient who has been using an antiviral nucleoside analogue, such as adefovir or lamivudine, for a long time, and the HBV genome is a drug-resistant HBV genome.

The amino acid mutation of the drug-resistant HBV genome is selected from the group consisting of rtA181V, rtN236T, rtL180M, rtM204V and a combination thereof in a reverse transcriptase region of the HBV genome, the numbers represent sites of the amino acid mutation, and the subsequent English letters are amino acids of the mutation. Preferably, the amino acid mutation of the drug-resistant HBV genome is selected from the group consisting of rtL 180M and rtM204V.

In a specific embodiment of the present invention, a miR-122 gene knock-out animal is provided. The endogenous miR-122 in the genome is knocked out. For the preparation method, please refer to J Clin Invest. 2012; 122 (8): 2884-2897.

The miR-122 knock-out animal provided by the present invention has partial or complete loss of expression on one or two of its alleles.

During the process of gene knock-out, the expression of the target gene may be reduced to an undetectable or insignificant level. The deletion of miR-122 means that the expression of miR-122 has been substantially reduced. This goal can be achieved in a variety of ways, including adding a destructive sequence to the target gene, such as inserting one or more stop codons, inserting a DNA fragment, deleting part of the target gene sequence, or using a stop code instead of general codons of the target gene. In addition, there are many different methods that can be used to achieve the effect of "gene knock-out", such as the deletion of part or all of a chromosome on which the original gene is located, including deletion of non-coding regions, especially promoter regions, 3'-end regulatory sequences, enhancers, or deletion of certain genes that can activate target gene expression. In addition, gene knock-out can also be achieved with an anti-sense artificial nucleotide to prevent target gene expression.

In addition, gene knock-out also includes conditional knock-out, such as exposing an animal to a substance that can cause a target gene to mutate, and adding an enzyme that can cause recombination of a target gene (such as Cre of the Cre-lox system) to achieve tissue or time-specific gene knock-out methods.

In a specific embodiment, the endogenous miR-122 is heterozygous knock-out or homozygous knock-out. Preferably, the endogenous miR-122 is heterozygous knock-out.

In a specific embodiment of the present invention, a non-human transgenic animal is provided, which has a genome encoding an HBV genome and the endogenous miR-122 knock-out. The non-human transgenic animal is produced by hybridizing the aforementioned non-human transgenic animal expressing hepatitis B virus and an endogenous miR-122 knock-out animal.

The non-human transgenic animal of the present invention can be used as an animal model for hepatocellular carcinoma. In particular, these animals can be used to evaluate the efficacy of compounds or compositions for treating or preventing hepatocellular carcinoma. Evaluation is carried out by administering a test compound or composition to a non-human transgenic animal of the present invention, or contacting the test compound or composition with an organ (such as liver), tissue, or cells (such as liver cells) derived from the non-human transgenic animal, and then determining the therapeutic effect of the test compound or composition on the hepatocellular carcinoma in organs, tissues or cells of the non-human transgenic animal. For example, clinically pathological determination of cancer size can be used to evaluate non-human transgenic animals. A test compound or composition that can alleviate the symptoms of cancer may be effective in treating or preventing hepatocellular carcinoma.

Features of the invention also include expression vectors suitable for producing the non-human transgenic animals of the invention. The expression vector includes a promoter operably linked to a nucleic acid encoding a hepatitis B virus to mediate its expression in the liver or other organs or tissues.

In addition, since the aforementioned non-human transgenic animal, which has a genome encoding the HBV genome and the endogenous miR-122 knock-out, has an early and high incidence of spontaneous hepatocellular carcinoma and abnormal fat metabolism, the present invention also provides use of miR-122 for preparing a medicament for preventing or treating hepatocellular carcinoma, wherein the medicament effectively improves endogenous miR-122 of an individual in need.

EXAMPLES

Figure 3:
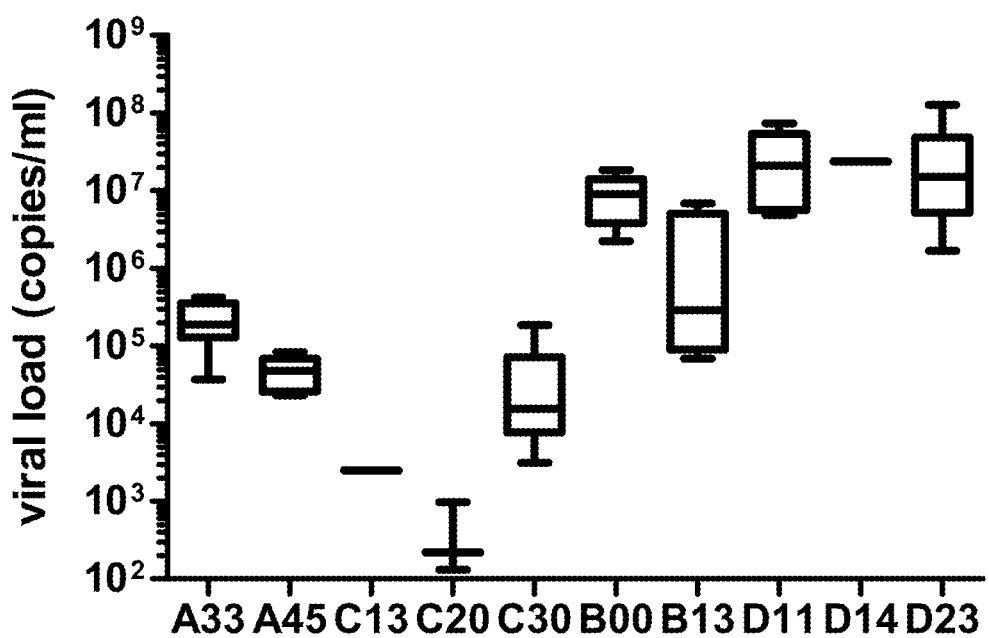
FIG. 3 shows the amount of HBV virus measured in the serum of 3-month-old HBV transgenic mice of various strains, of which the virus amount of adefovir wild-type/drug resistant strains (C13, C20, C30/A19, A33, A45) is between 10E+2~10E+5, and the virus amount of lamivudine wild type/drug resistant strains (D11, D14, D23/B00, B13) is between 10E+5~10E+8.

Example 1 Simulated Human Hepatocellular Carcinoma with a High Amount of Hepatitis B Virus and Down-Regulated miR-122, without Addition of a Chemical Carcinogen, has a High Incidence of Hepatocellular Carcinoma Based on the understanding of human and animal hepatocellular carcinoma patterns, HBV DNA from HBV virus particles were isolated from blood in the present invention (Table 1: D14 and D23, nuclear promoter mutants are common in HCC, and genotype B is the major genotype of hepatitis B virus in Taiwan) [A19, A33, and A45 strain mice contain Adefovir resistant HBV DNA (SEQ ID NO: 1); B00 and B13 strain mice contain lamivudine resistant HBV DNA (SEQ ID NO: 2); C13, C20, and C30 strain mice contain DNA of wild-type HBV that is sensitive to Adefovir (SEQ ID NO: 3); D11, D14 and D23 strain mice contain DNA of wild-type HBV that is sensitive to lamivudine (SEQ ID NO: 4)], establishing HBV genome with 1.46 times the length containing Enhancer I and Enhancer II at the 5' end to polyadenylation site (Poly A) at the 3' end. The HBV genome can fully transcribe HBV mRNA such as pregenomic/precore, large/middle/small HBs and HBx. The 1.46 times length of the HBV genome was connected to a mouse albumin promoter at the 5' end and a chicken HS4 insulators at the 3' end (SEQ ID NO: 5) to form a 10.4 Kb HBV transgenic gene (FIG. 1). Hepatitis B virus transgenic mice were then crossed with miR-122 knock-out mice to produce hybrid mice similar to patients with human hepatitis B and hepatocellular carcinoma. The expression level of miR-122 in the hybrid mice is lower than that of normal mice because it has only a single set, and express a large number of HBV viruses. As the mice got older, miR-122 decreases further. Compared with the general HBV gene transgenic mice, this hybrid mouse has an earlier and higher incidence of spontaneous hepatocellular carcinoma, and the incidence of hepatocellular carcinoma in male mice is 60~90%, which is more suitable for study of hepatocellular carcinoma prevention or treatment (FIG. 3 and Table 2). Table 2 clearly shows that the combination of high-hepatitis B virus load and a single set of miR-122 significantly increased the incidence of hepatocellular carcinoma in the hybrid mice: B6 wild-type mice do not develop hepatocellular carcinoma, and a single set of miR-122 mice also rarely develop hepatocellular carcinoma. The incidence of hepatocellular carcinoma is not high in pure hepatitis B virus transgenic mice, especially D23 strains and female mice. However, hybrid mice of the mice with high hepatitis B virus load and the mice with a single set of miR-122 have significantly increased incidence of hepatocellular carcinoma without the need of addition of any chemical carcinogen. The characteristic of high incidence of hepatocellular carcinoma in the hybrid mice established by the present invention was repeatedly shown in four generations of mice over eight years, proving that this mouse strain is a stable animal model for hepatocellular carcinoma, and suitable for basic and translational studies of hepatocellular carcinoma. The reproduction cost of the mouse strain is also low, which is suitable for the animal model for hepatocellular carcinoma.

TABLE 1

Isolation of HBV strains from patient blood to establish HBV transgenic mice

| Clone | Diagnosis | Resistance | Mutation in BCP | Mutation in RT | Genotype | Strain of Tg mice |
|---|---|---|---|---|---|---|
| M8817 | HCC-B | No resistance | A1762T G1764A | rtA181A rtN236N | C | C13, C20, C30 |
| P3257 | HCC-B | Adefovir (ADV) | A1762T G1764A | rtA181V rtN236T | C | A19, A33, A45 |
| M1840 | CHB | No resistance | A1762T G1764A | rtL181L rtM236M | B | D11, D14, D23 |
| P3358 | CHB | 3TC (LAM) | A1762T G1764A | rtL181M rtM236V | B | B00, B13 |

Note: Four hepatitis B virus strains (M8817, P3257, M1840, P3358) came from two patients, of which M8817 and P3257 came from the serum samples of a hepatocellular carcinoma patient (HCC-B) before using the anti-drug Adeforvir (ADV) and after having drug resistance to Adeforvir, respectively. Virus strains M1840 and P3358 were obtained from serum samples of a patient with chronic hepatitis B (CHB)

before using the antiviral drug lamivudine (LAM, 3TC) and after having drug resistance to lamivudine. Gene mutations of basal core promoter (BCP) of HBV that are common among patients with hepatocellular carcinoma and gene mutation sites of reverse transcriptase (RT) of HBV that are common among patients with long-term use of antiviral drugs ADV and LAM are analyzed in the table.

TABLE 2

Incidence of hepatocellular carcinoma (after 18 months old)

| Group | Lineage | genotype | Male | Female |
| --- | --- | --- | --- | --- |
| B6 | B6 | 122+/+ | 0% (0/29) | 0% (0/25) |
| HBV Tg | D23 | D23; 122+/+ | 12% (3/25) | 15% (4/26) |
| | D14 | D14; 122+/+ | 44% (12/27) | 40% (14/35) |
| miR-122+/− | 122+/− | 122+/− | 0% (0/12) | 7% (1/15) |
| Hybrid | D23122 | D23; 122+/− | 85% (17/20) | 42% (5/12) |
| | D14122 | D14; 122+/− | 92% (23/25) | 86% (18/21) |

Figure 4:
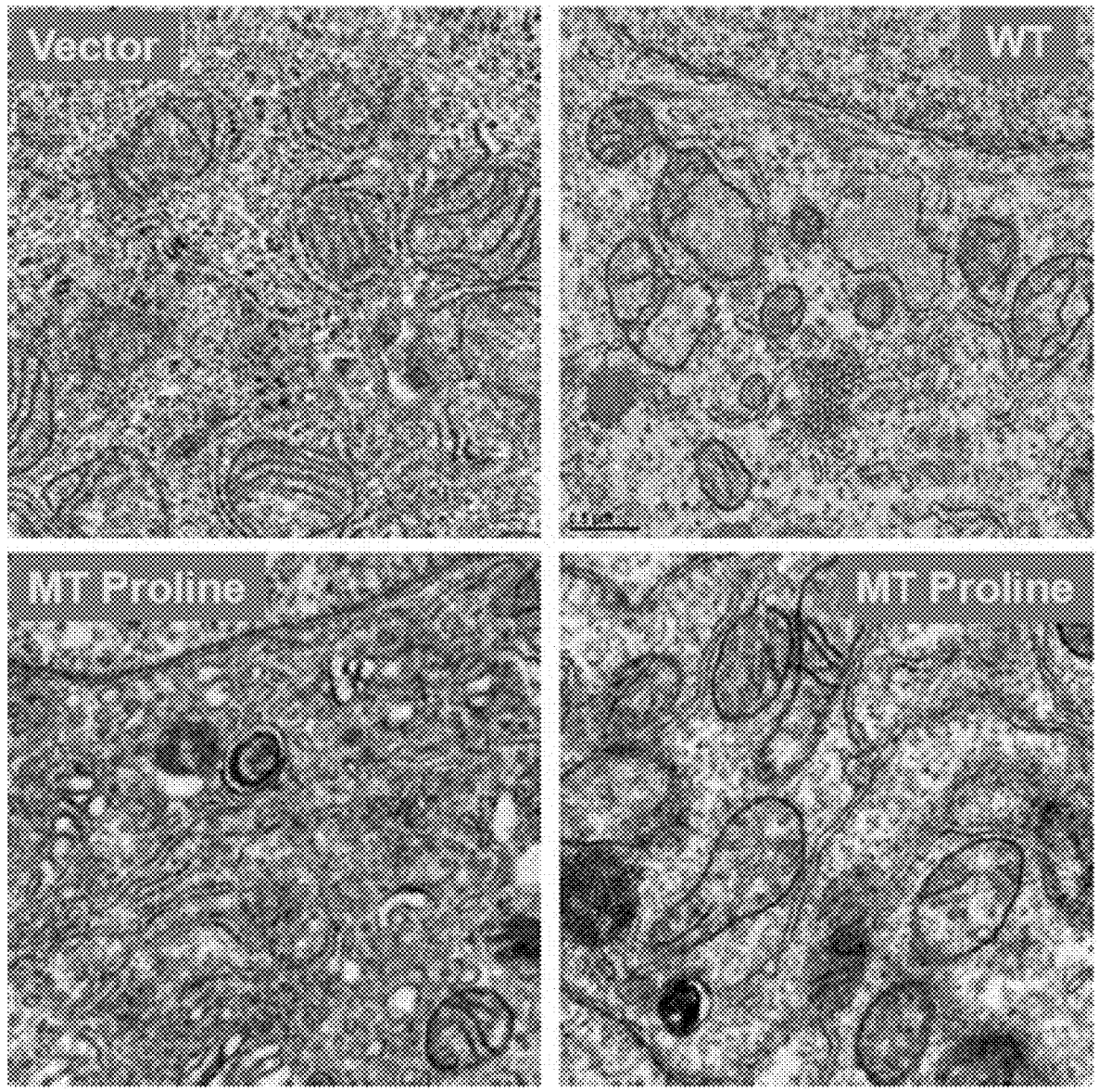
FIG. 4 shows changes in the shape and function of mitochondria in hepatoma cells transfected with the hepatitis B virus-expression vector. Vector, human cell line Huh-7 transfected with blank vector; WT, human cell line Huh-7 transfected with wild-type hepatitis B virus; MT Proline, human cell line Huh-7 transfected with preS2 knock-out mutant hepatitis B virus.
Figure 5:
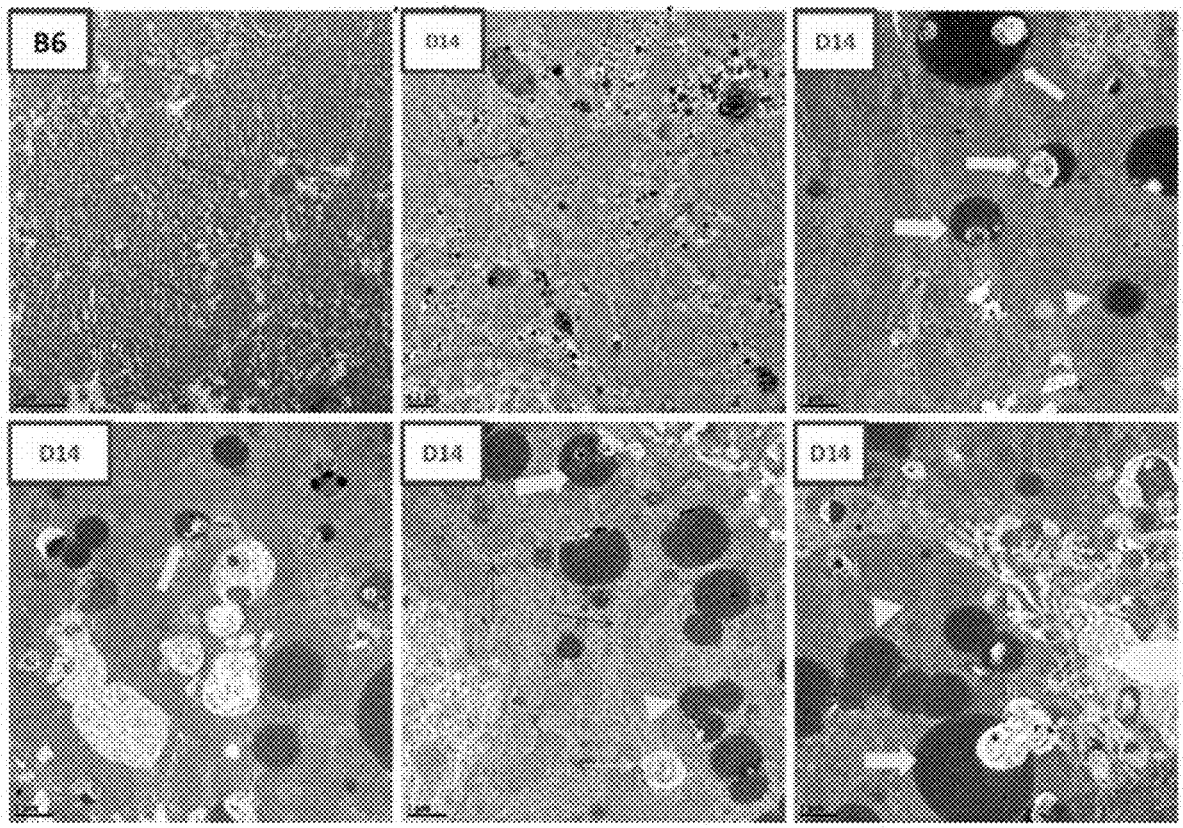
FIG. 5 shows that the mitochondria of the hepatitis B virus transgenic mice changed within five months, with more mitochondria shattered into small granules, lysosomes, autophagolysosomes, and autophagic vacuoles. The yellow arrows indicate autophagolysosomes, the yellow triangles indicate lysosomes, and red arrows indicate mitochondria.
Figure 6:
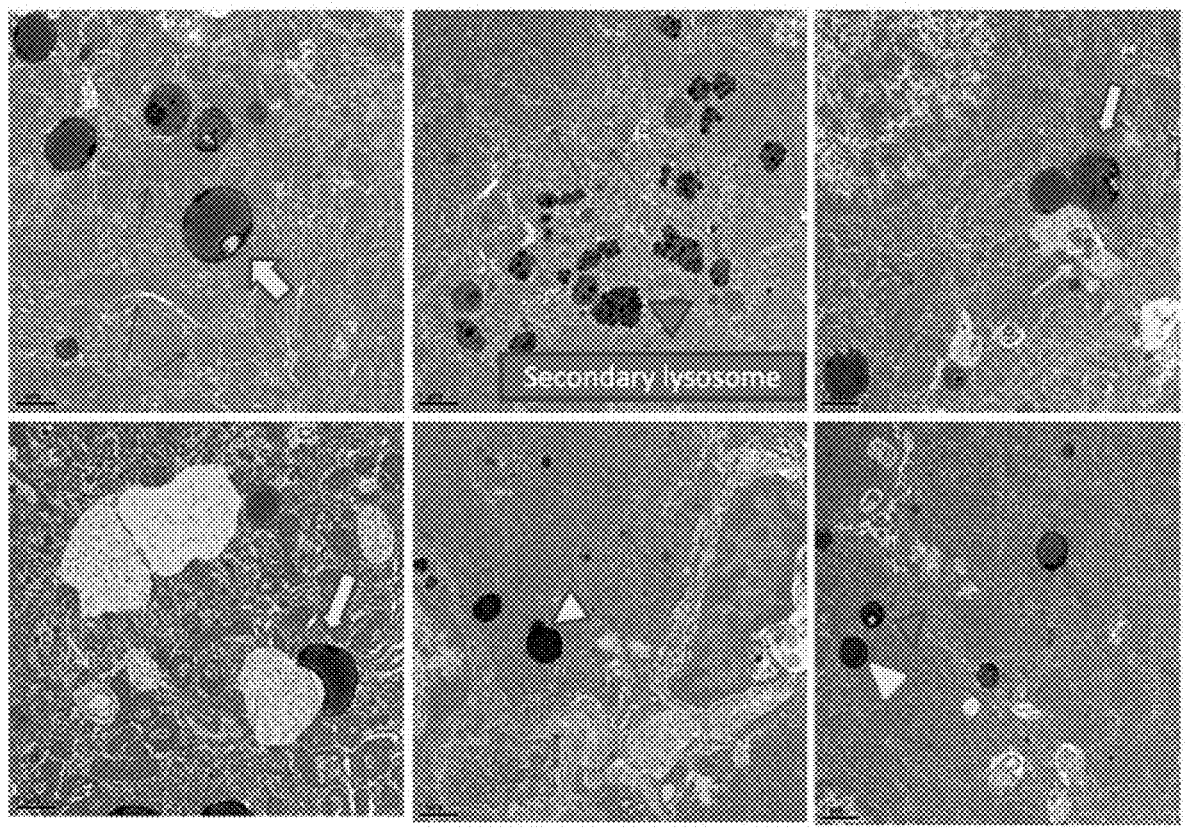
FIG. 6 shows that the mitochondria of a hybrid mouse hybridized with a hepatitis B virus transgenic mouse and an miR-122 knock-out mouse changed within five months, with more mitochondria shattered into small granules, lysosomes, autophagolysosomes, and autophagic vacuoles. When the hybrid mouse was 5-6 months old, there was a lot of autophagy in liver tissue. The yellow arrows indicate autophagolysosomes, the yellow triangles indicate lysosomes, the red arrows indicate mitochondria, and the blue arrows indicate secondary lysosomes.
Figure 7:
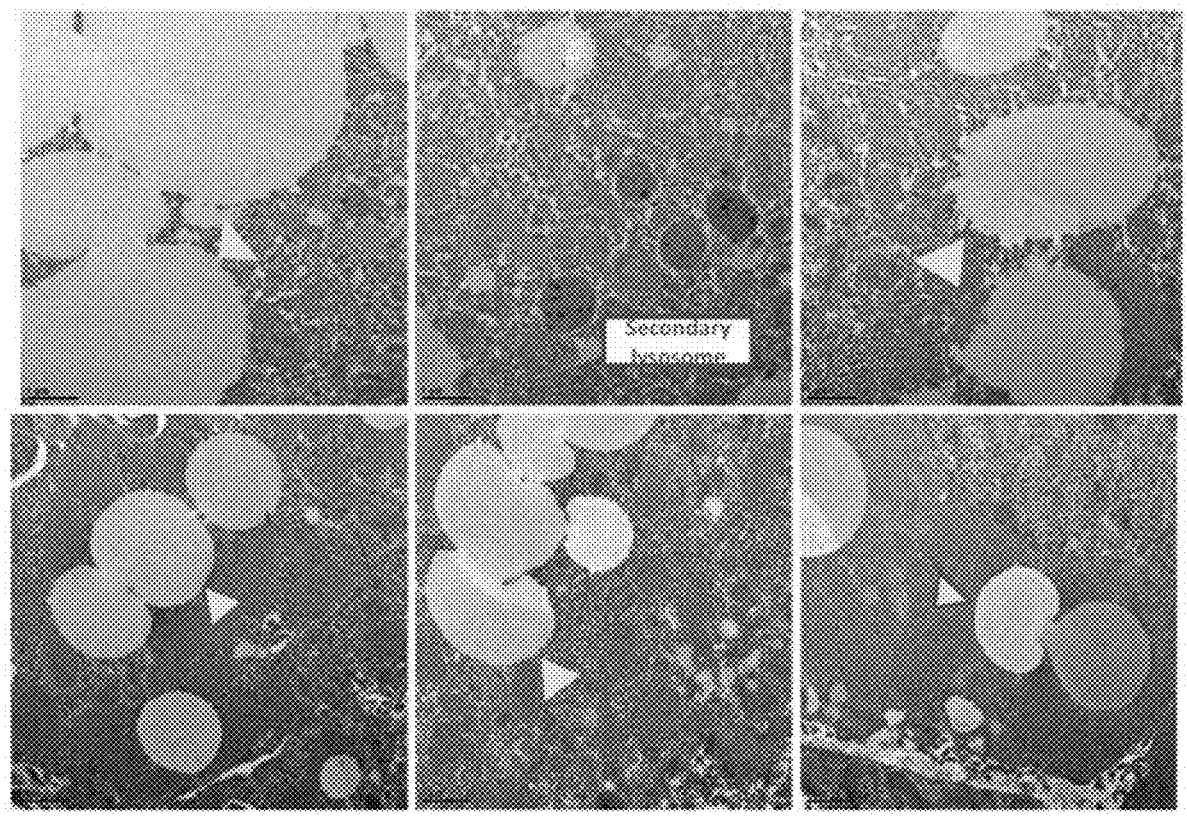
FIG. 7 shows the liver tissue of a hybrid mouse hybridized with a hepatitis B virus transgenic mouse and a miR-122 knock-out mouse under a transmission electron microscope. The mitochondria in liver cells changed when the mouse was five months old, with more mitochondria shattered into small granules, lysosomes, autophagolysosomes, autophagic vacuoles, and fatty oil droplets. When the hybrid mouse was 5-6 months old, there was fat accumulation in the liver and a lot of autophagy in the liver tissue. The yellow arrows indicate autophagolysosomes, the yellow triangles indicate lysosomes, the red arrows indicate mitochondria, and the blue arrows indicate secondary lysosomes.
Figure 8:
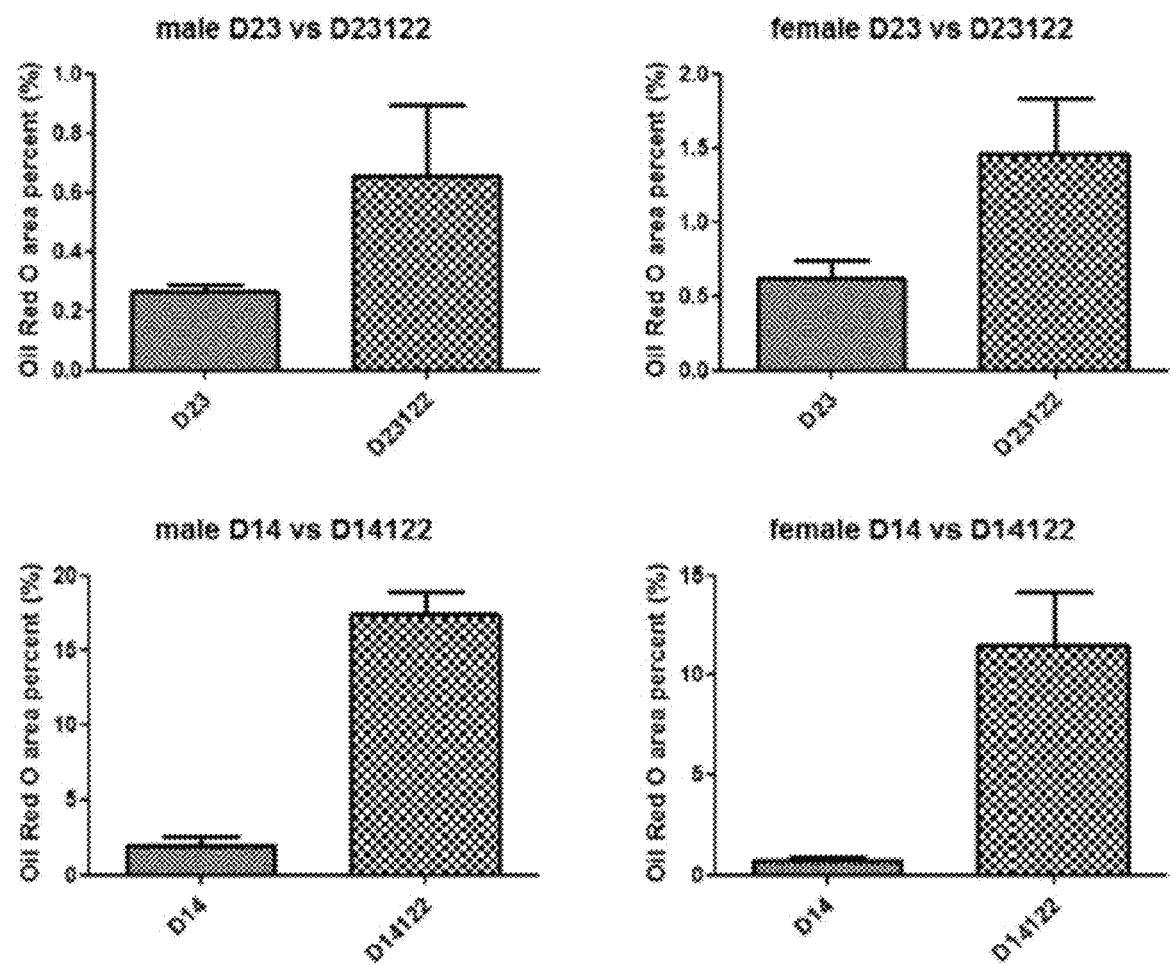
FIG. 8 shows that the liver of the hybrid mouse has more neutral fat accumulation. Oil Red stains the neutral fatty acids in oil droplets to red. Mouse liver tissues were embedded in OCT, frozen, sliced, and then stained with Oil Red, and were photographed and observed with an optical microscope. Images were analyzed with the software Image J to quantify Oil Red staining per unit area of the tissues. The neutral fat distribution in the liver tissues of 6-month-old male and female HBV transgenic mice D14, D23 and the hybrid mice D14122, D23122 were compared respectively. The neutral fat distribution in the liver tissues of the two hybrid mice (D14122, D23122) was significantly higher than that of the HBV transgenic mice (D14, D23), showing a phenomenon similar to fatty liver in patients with chronic hepatitis B infection.

Example 2 Changes in the Shape and Function of Mitochondria in the Liver Tissue of Hepatitis B Virus Transgenic Mice and Hybrid Mice Hepatitis B virus can cause changes in the shape and function of mitochondria in the liver of patients with chronic hepatitis B, and miR-122 can also be down-regulated by hepatitis B virus. Shape and function of mitochondria in hepatoma cell lines which were transfected with hepatitis B virus-expressing vectors changed as those of mitochondria in liver of patients with chronic hepatitis B (FIG. 4). The shape of mitochondria in liver tissues of hepatitis B virus transgenic mice and the hybrid mice established by the present invention changed with more mitochondria shattered into small granules, lysosomes, autophagolysosomes, and autophagic vacuoles (FIG. 5, FIG. 6, and FIG. 7). Fatty oil droplets were accumulated in the liver tissue of the hybrid mice (FIG. 7 and FIG. 8).

Figure 9A:
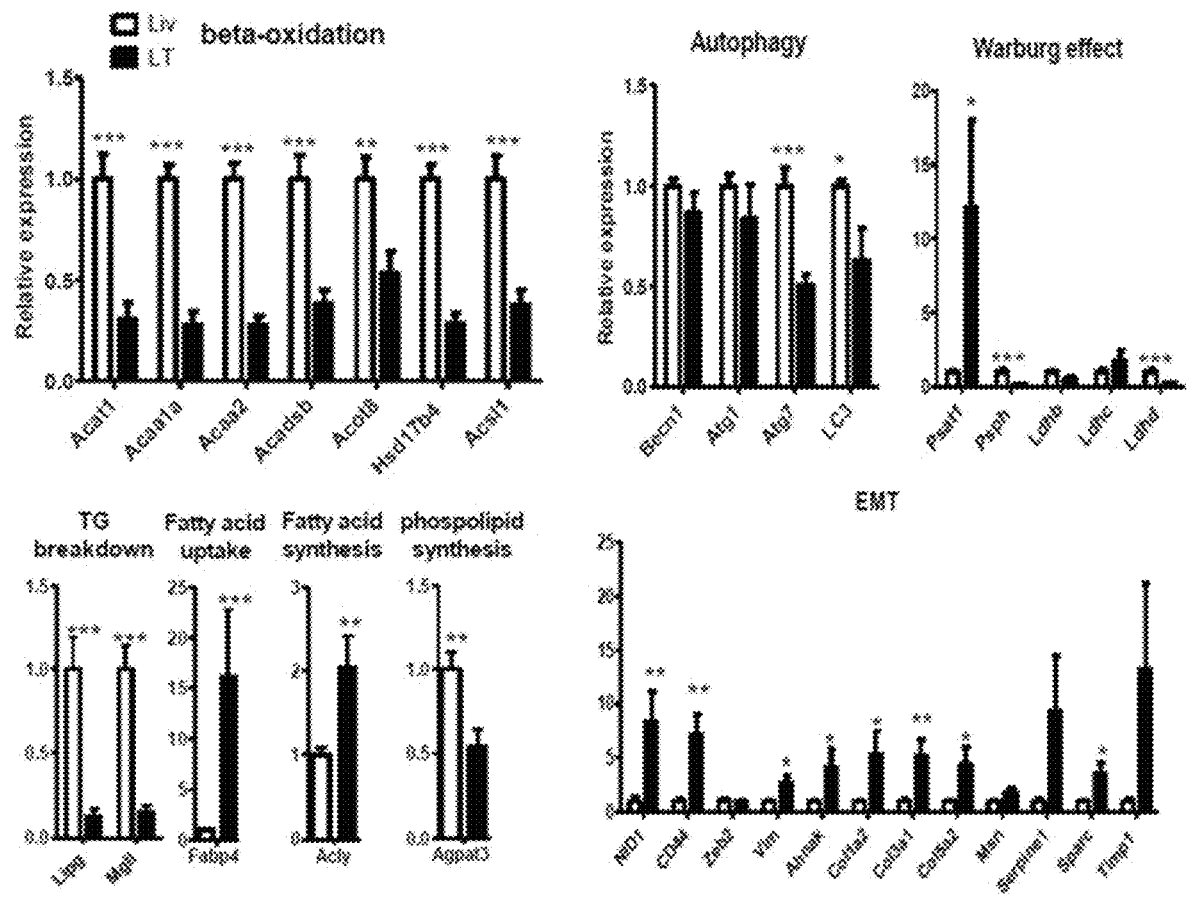
FIG. 9A shows the analysis of gene expression in which RNA of hepatocellular carcinoma tissue (LT) of 11 HBV transgenic mice and RNA of normal liver tissue (Liv) of 11 B6 mice were extracted, reverse transcribed into cDNA, and analyzed using Real-Time PCR (qPCR). The results show that the expression of genes related to fatty acid beta-oxidation, triglyceride cleavage, autophagy, phospholipid synthesis decreased, whereas the expression of genes related to fatty acid synthesis, fatty acid uptake, and EMT increased.
Figure 9B:
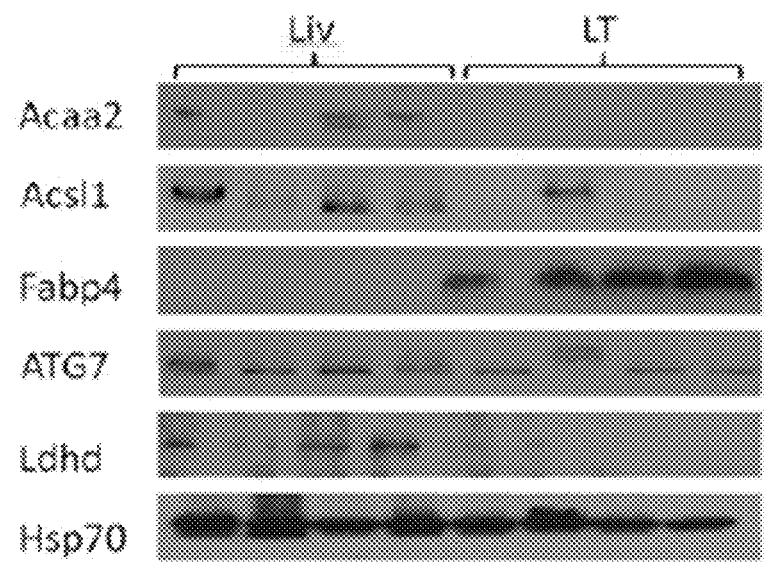
FIG. 9B shows the protein expression of related genes using Western Bolting. It was also found that the expression of the genes related to fatty acid beta-oxidation, Acaa2 and Acsl1, decreased, the expression of the gene related to autophagy, Atg7, decreased, and the expression of the gene related to fatty acid uptake, Fabp4, increased.
Figure 9B:
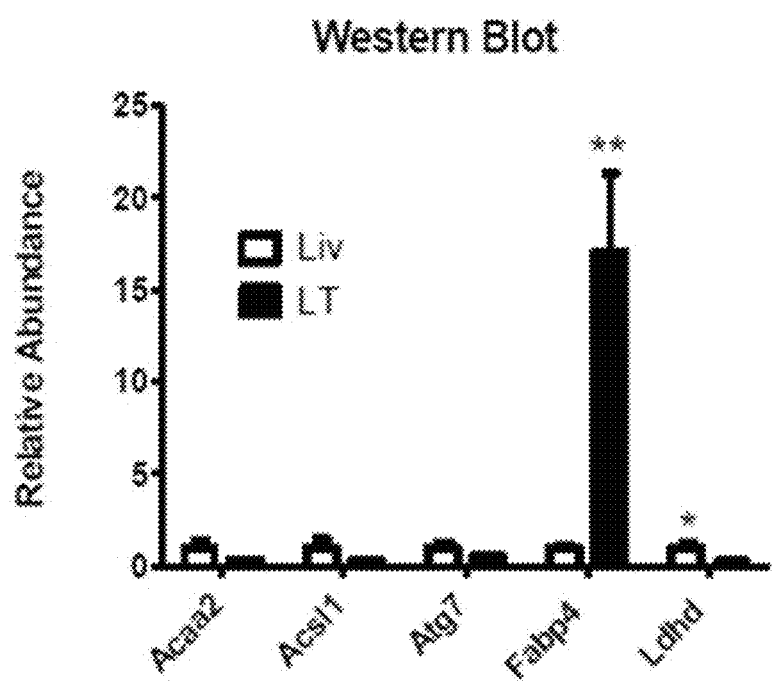

Example 3 Characteristics of Gene Expression of Liver Tissues of Hepatitis B Virus Transgenic Mice and the Hybrid Mice The gene expression differences between the tumors of hepatitis B virus transgenic mice and normal liver tissues of B6 mice were systematically investigated. Differentially expressed genes (DEG) of tumors of the hepatitis B virus transgenic mice and normal liver tissues of B6 mice were analyzed by microarray. Using Limma of Bioconductor R to analyze DEGs of hepatocellular carcinoma tissues and normal liver tissues, under the threshold of p<0.01, 1003 probe sets (756 genes) were screened and showed significant changes, of which 483 probe sets were upregulated, corresponding to 364 genes, and 520 probe sets were down-regulated, corresponding to 395 genes. Among the top ten pathways with the most significant differences in down-regulated genes, genes related to fatty acid beta oxidation, bile acid synthesis, retinoic acid synthesis, androgen and estrogen synthesis declined significantly. Signaling-related genes such as integrin signaling and 14-3-3 related signaling increased. RNA of hepatocellular carcinoma tissue (LT) of 11 HBV transgenic mice and RNA of normal liver tissue (Liv) of 11 B6 mice were extracted, reverse transcribed into cDNA, and the expression of genes is analyzed using Real-Time PCR (qPCR). The results show that the expression of genes related to fatty acid beta-oxidation, triglyceride cleavage, autophagy, phospholipid synthesis decreased, whereas the expression of genes related to fatty acid synthesis, fatty acid uptake, and EMT increased (FIG. 9A). Protein expression of related genes was analyzed using Western Bolting. It was also found that the expression of the genes related to fatty acid beta-oxidation, Acaa2 and Acsl1, decreased, the expression of the gene related to autophagy, Atg7, decreased, and the expression of the gene related to fatty acid uptake, Fabp4, increased (FIG. 9B).

Figure 10:
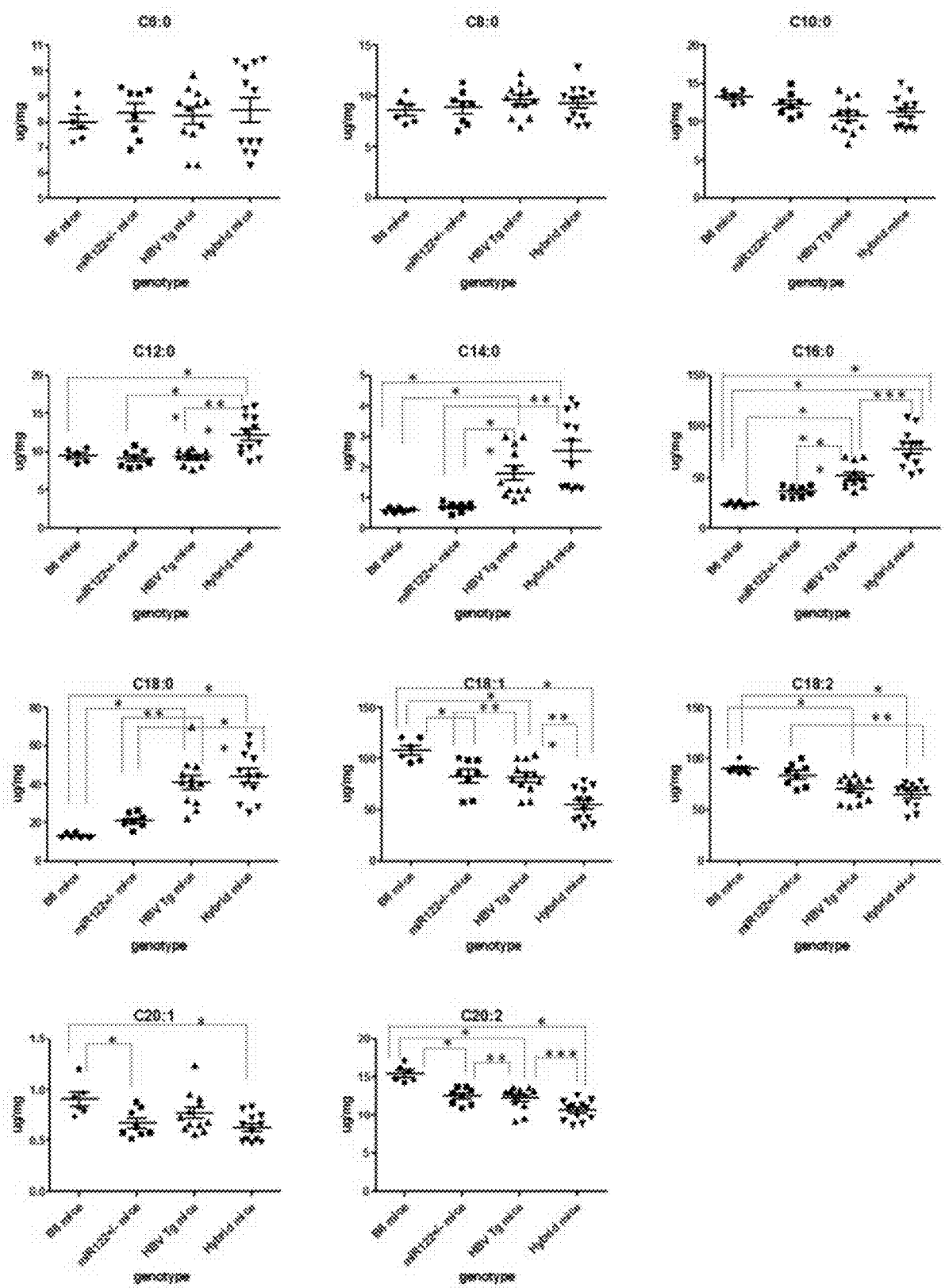
FIG. 10 shows that the composition of saturated fatty acids increased and unsaturated fatty acids decreased in the early stage of livers of the HBV transgenic mice and the hybrid mice. In order to compare the fatty acid composition in the early stage of livers of mouse strains with different tumor incidences, liver tissue extracts of 6 months old B6 mice (3 males and 3 females), miR-122+/− mice (4 males, 4 females), HBV transgenic mice (3 males and 3 females of D14; 3 males and 3 females of D23), and the hybrid mice (3 males and 3 females of D14122; 4 males and 3 females of D23122) were quantitatively analyzed for fatty acid content (microgram fatty acids/milligram liver tissue) by GC-MS. Tukey's multiple comparison test of the ONE way ANOVA test was use to determinate significant differences. * $P<0.05$,  $P<0.01$, * $P<0.001$.

Example 4 Abnormal fat Metabolism in Liver Tissues of Hepatitis B Virus Transgenic Mice and the Hybrid Mice In order to further compare the fatty acid composition in the early stage of livers of mouse strains with different tumor incidences, liver tissue extracts of 6 months old B6 mice (3 males and 3 females), miR-122+/− mice (4 males, 4 females), HBV transgenic mice (3 males and 3 females of D14; 3 males and 3 females of D23), and the hybrid mice (3 males and 3 females of D14122; 4 males and 3 females of D23122) were quantitatively analyzed for fatty acid content (microgram fatty acids/milligram liver tissue) by GC-MS. The results showed that the composition of saturated fatty acids increased and unsaturated fatty acids decreased in the early stage of livers of the HBV transgenic mice and the hybrid mice (FIG. 10). It has been shown that mitochondrial abnormalities caused by hepatitis B virus and abnormal fat metabolism caused by miR-122 down-regulation are closely related to the occurrence of hepatocellular carcinoma.

Figure 11A:
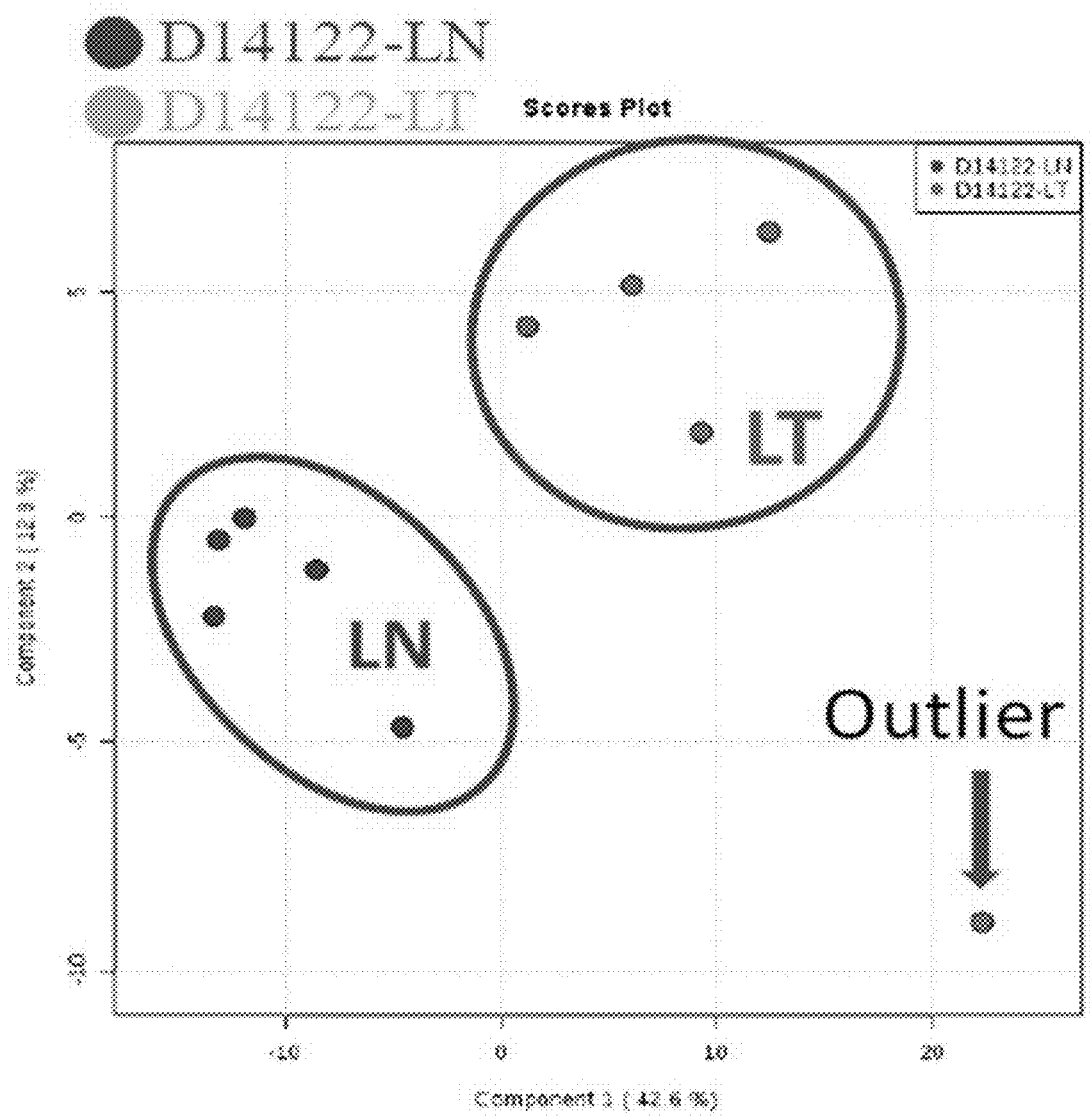
FIGS. 11A-11C show comparisons of NMR analysis of hepatocellular carcinoma tissues and non-cancerous tissue metabolites in hybrid mice with hepatocellular carcinoma.
Figure 11B:
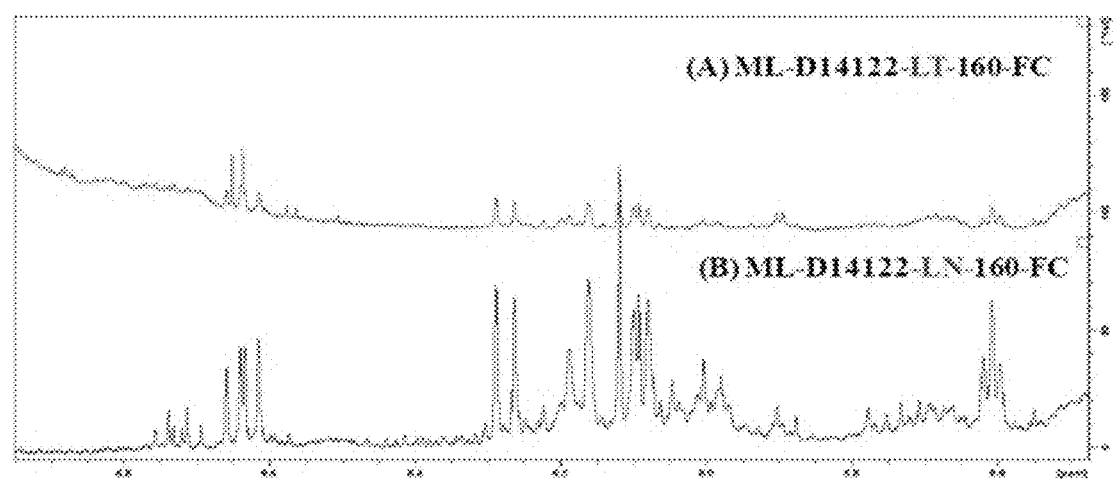
Figure 11C:
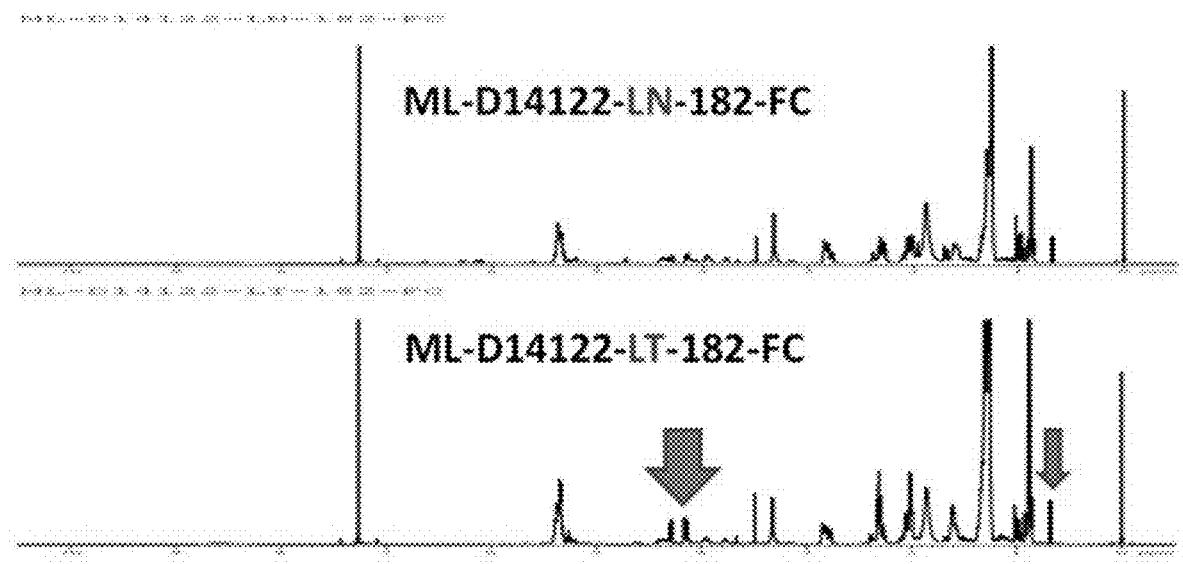

FIGS. 11A-11C show comparisons of NMR analysis of hepatocellular carcinoma tissues and non-cancerous tissue metabolites in mice with hepatocellular carcinoma (hybrid tumor). Partial least squares discriminant analysis plot (PLS-DA score plot) showed that fat-soluble metabolites in hepatocellular carcinoma tissues and non-cancer tissues were clearly grouped (FIG. 11A). FIG. 11B shows that the chemical shift in the region between 5.6-6.8 ppm of hepatocellular carcinoma tissue is a decrease in olefinic protons (b-carotene, vitamin A, and retinoic acid) of conjugated polyenes. Comparison between hepatocellular carcinoma tissue (ML-D14122-LT-182-FC) and non-cancer tissue (D14122-LN-182-FC) shows that the content of triglyceride and cholesterol was higher in hepatocellular carcinoma tissues, and the content of polyunsaturated fatty acids was lower in hepatocellular carcinoma tissue, which may be caused by a decrease in de novo synthesis of lipid in hepatocellular carcinoma tissues (FIG. 11C). The decrease of tumor suppressor molecules b-carotene, vitamin A, retinoic acid, and miR-122 may be closely related to the generation of hepatocellular carcinoma. Clinical reports show that chronic hepatitis B carriers with diabetes, fatty liver, or metabolic syndrome increase the risk of cirrhosis and hepatocellular carcinoma, but the reasons are unknown. The hepatitis B virus transgenic mice and their hybrid provided by the present invention are excellent models for mechanism and translation research for development of effective measures and treatments.

Example 5 Down-Regulation of miR-122 of Hepatitis B Virus Transgenic Mice and the Hybrid Mice were Used to Develop Biomarkers of Hepatocellular Carcinoma The hybrid mice were born with only a single set of miR-122. As the mice got older, hepatitis B virus in the mice further down-regulated miR-122. After the formation of hepatocellular carcinoma, miR-122 in cancer tissues was further reduced. Both mitochondria and miR-122 play a key role in the metabolic balance of fat. The abnormal function of both will cause the accumulation of liver fat and form a non-alcoholic fatty liver disease that affects human health worldwide. When the hybrid mouse of the present invention was 5-6 months old, there was fat accumulation in the liver and a lot of autophagy in the liver tissue. Microarray analysis showed increased fat synthesis, decreased metabolism and decomposition, increased epidermal interstitialization of hepatocellular carcinoma tissues, decreased beta oxidation of fats, and decreased vitamin A and retinoic acid in cancer tissues. Therefore, the hybrid mice of the present invention can be used as a development tool of biomarkers for diagnosis of early stage of hepatocellular carcinoma.

Figure 12A:
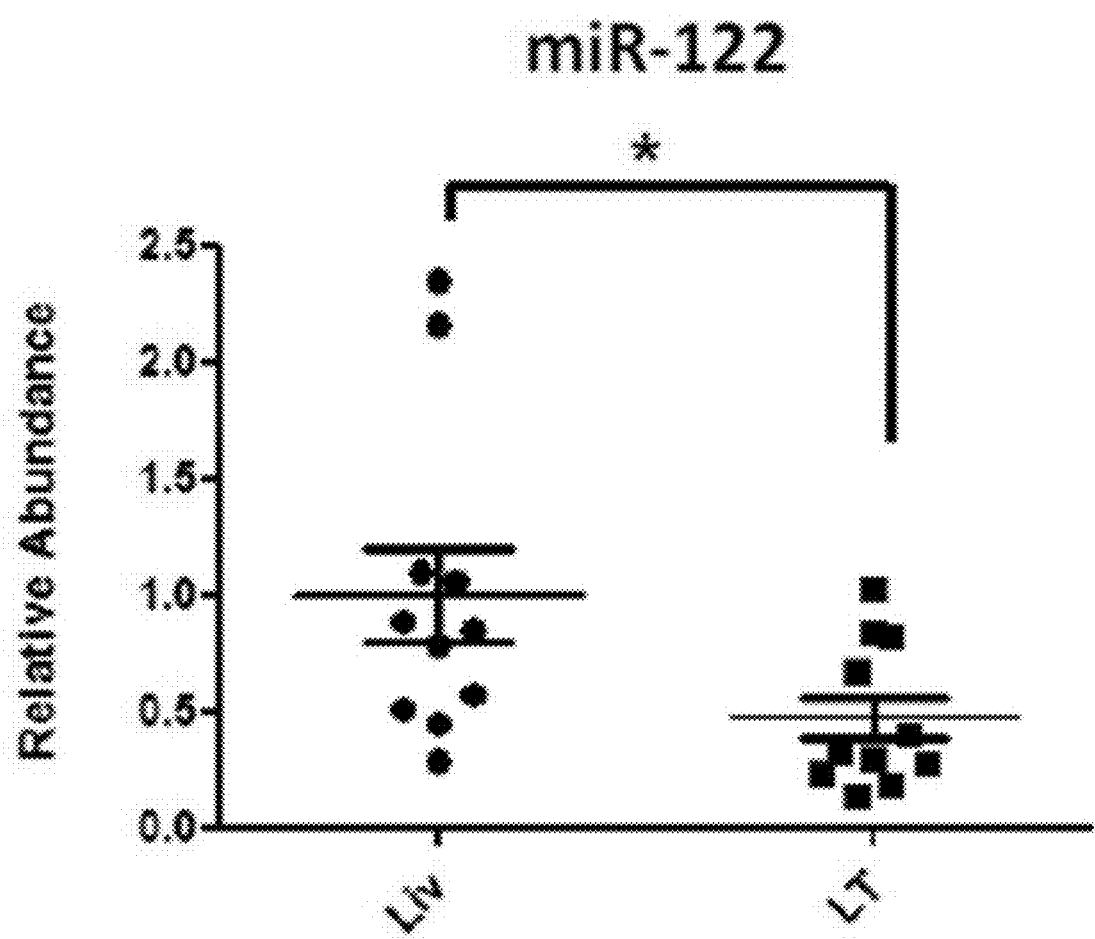
FIGS. 12A-D show that the hybrid mice were used as a biomarker development tool for early hepatocellular carcinoma diagnosis.
Figure 12B:
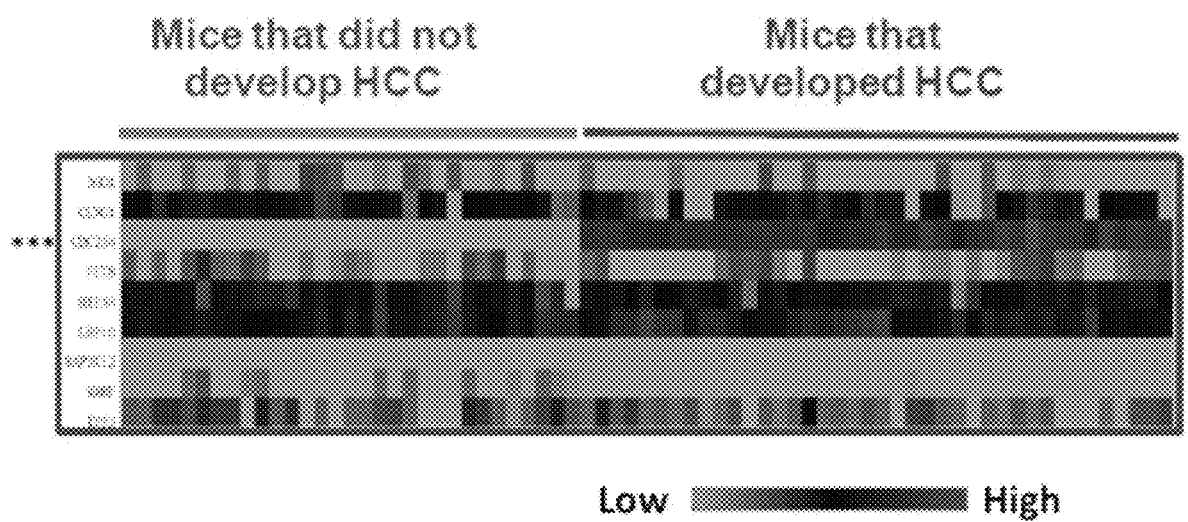
Figure 12C:
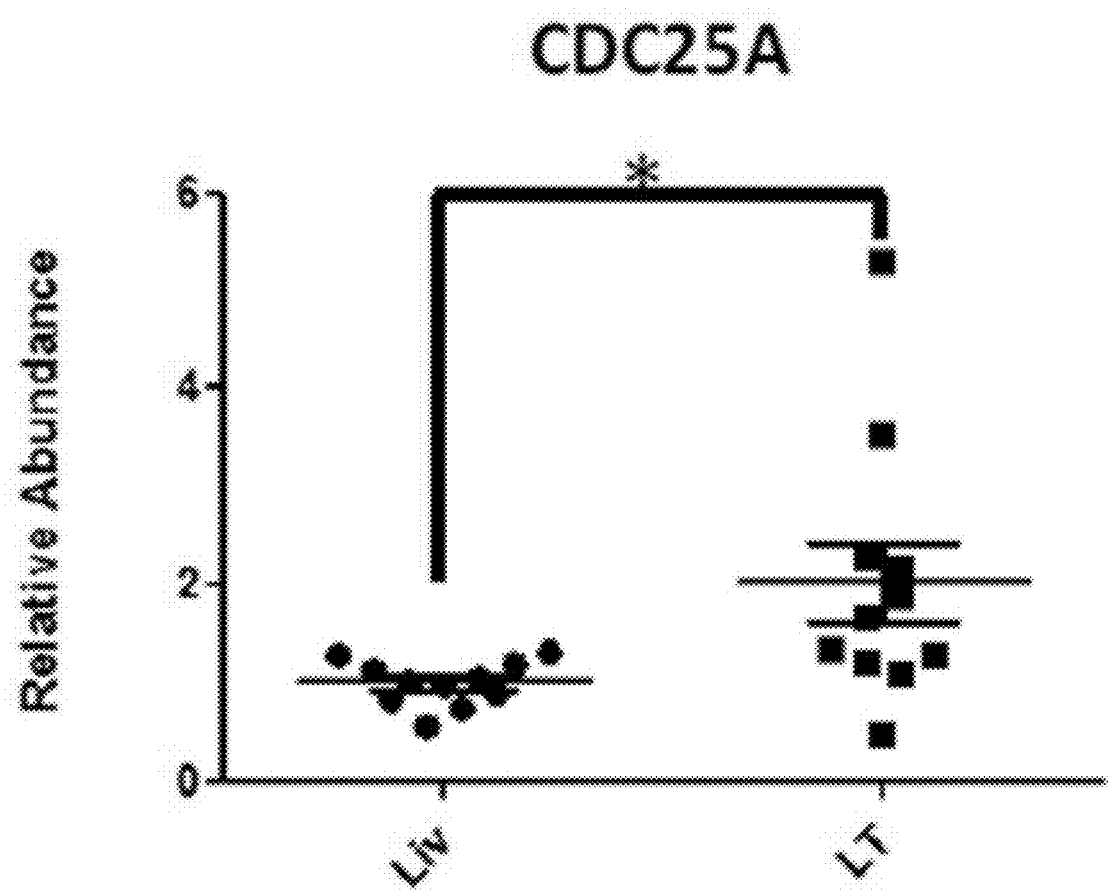
Figure 12D:
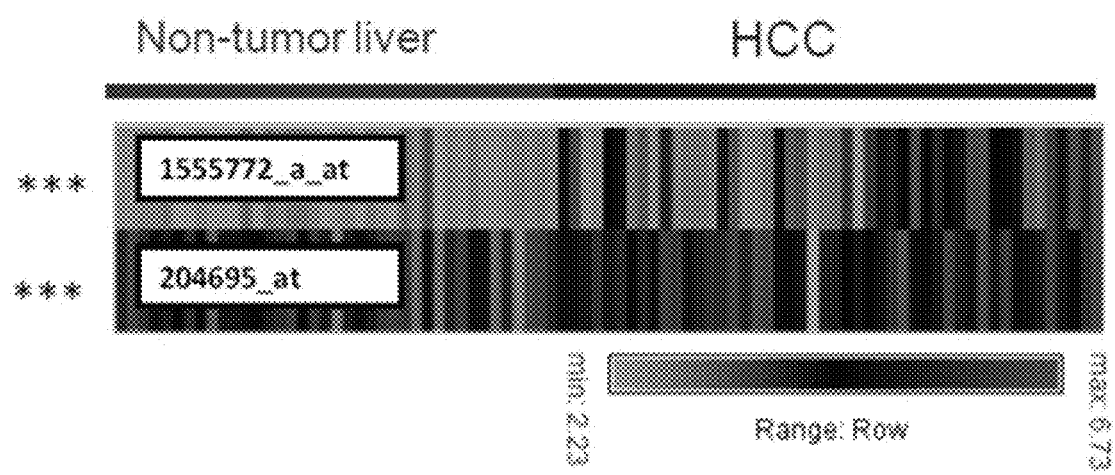

An example is provided herein. First, the measurement shows that liver miR-122 expression was lower in hepatocellular carcinoma tissues of HBV transgenic mice (LT, N=11) than in normal liver tissues of B6 mice (Liv, N=11) (FIG. 12A). The "case-control study" was used to distinguish hepatocellular carcinoma (43 mice, 25 males and 18 females) from non-cancer (32 mice, 11 females and 21 females) from hybrid mice older than 18 months. Blood samples of the early stage (4-8 months old) of the mice were compared to examine 9 possible miR-122 target genes, and the results indicated that CDC25A was significantly higher in the cancer group than that in the non-cancer group (FIG. 12B). The comparison of the expression of CDC25A gene in liver tissues indicates that the expression in hepatocellular carcinoma tissues (LT, from 11 HBV transgenic mice) is higher than that in normal liver tissues (Liv, from 11 B6 mice) (FIG. 12C). Gene expression of CDC25A in human HCC surgical specimens was further detected. Gene expression levels were extracted from the public domain of the dataset GSE45267 in the Gene Expression Omnibus (GEO) database, including RNA expression profiles of 48 HCC tissues and 39 non-tumor liver tissues, using Affymetrix Human Genome U133 Plus 2.0 gene expression microarray detection. The data related to the two CDC25A RNA detection probe sets (1555772_a_at and 204695_at) were extracted and displayed as a heat map using the generalized correlation map software. The expression of CDC25A was significantly higher in hepatocellular carcinoma tissues than that in non-cancer tissues (FIG. 12D). Therefore, decrease of miR-122 and increase of CDC25A can be used as markers for diagnosis of hepatocellular carcinoma.

Figure 13:
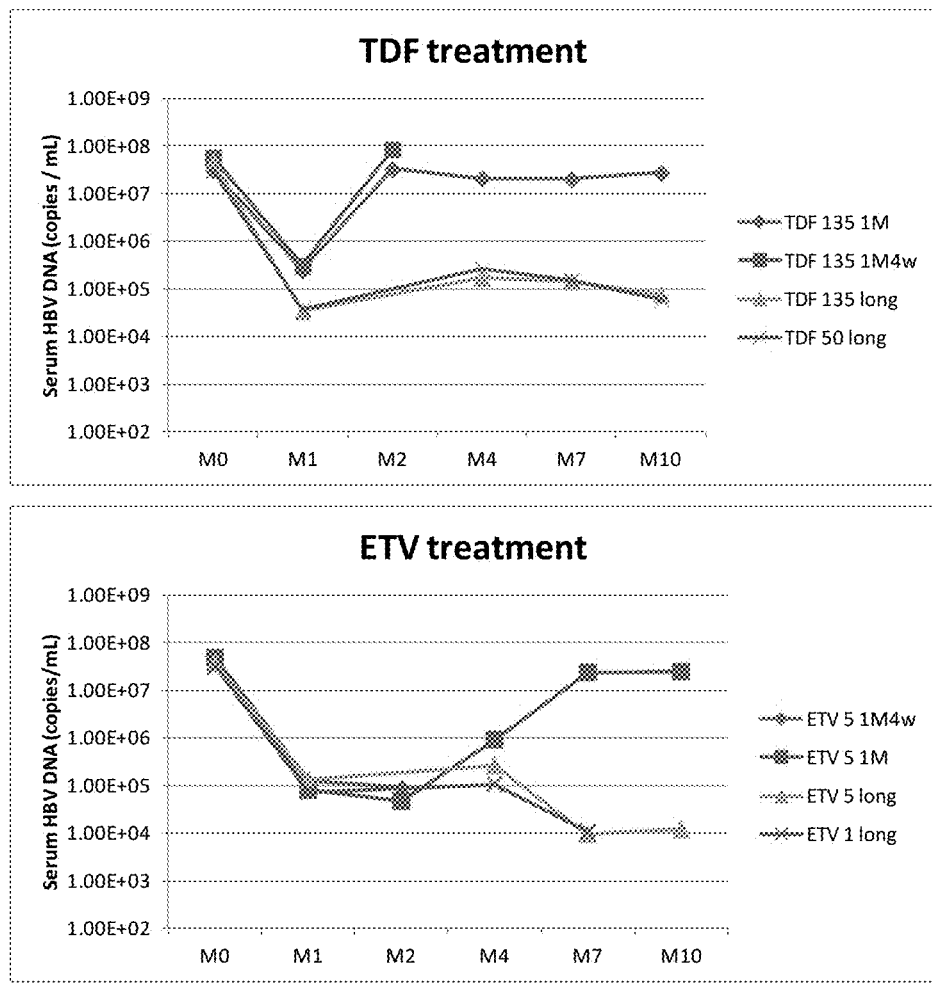
FIG. 13 shows the comparison of the effect of long-term use and withdrawal of HBV antiviral drug tenofovir (TDF) and entecavir (ETV) on viral load. Six-month-old hybrid mice were fed with different doses of TDF (135 or 50 mg/kg-day) and TEV (5 or 1 mg/kg-day). Both TDF and ETV can reduce the amount of virus to a minimum after one month of medication (M1). The amount of virus quickly rose to the level before medication (M0) after one month of withdrawal of TDF (M2), whereas the amount of virus maintained at the lower level after one month of withdrawal of ETV (M2). After 3 months of withdrawal (M4), the amount of virus gradually increased from 1.0E+5 to 1.0E+6. After 6 months of withdrawal (M7), the amount of virus rose to the level before the medication (M0).

Example 6 Hepatitis B Virus Transgenic Mouse and the Hybrid Mice were Used for Study on Drugs against Hepatitis B Virus and Hepatoma Clinically, the analysis of the health insurance database shows that the use of nucleoside analogue can indeed significantly reduce the incidence of hepatocellular carcinoma, especially it is better for non-cirrhosis patients with chronic hepatitis B who are younger than 40 years old. (Wu & Wu et al. Gastroenterology 2014). At present, nucleoside analogues that are more commonly used clinically are tenofovir (TDF) and entecavir (ETV), which have strong antiviral efficacy and rarely have drug resistance. Reactivation of the virus and recurrence of hepatitis occurred more frequently and early after withdrawal of tenofovir (TDF) than after withdrawal of entecavir (ETV). Withdrawal of tenofovir (TDF) may sometimes cause liver failure for some unknown reason. The effect of long-term use and withdrawal of HBV antiviral drug tenofovir (TDF) and entecavir (ETV) on the amount of virus was compared. Six-month-old hybrid mice were fed with different doses of TDF (135 or 50 mg/kg) and ETV (5 or 1 mg/kg). Both TDF and ETV can reduce the amount of virus to a minimum after one month of medication (M1). The amount of virus quickly rose to the level before medication (M0) after one month of withdrawal of TDF (M2), whereas the amount of virus maintained at the lower level after one month of withdrawal of ETV (M2). After 3 months of withdrawal (M4), the amount of virus gradually increased from 1.0E+5 to 1.0E+6. After 6 months of withdrawal (M7), the amount of virus rose to the level before the medication (M0) (FIG. 13). Studies of efficacy and side effects of long-term use of tenofovir (TDF) or entecavir (ETV) on reducing hepatitis by using the hybrid mice are going on, and valuable clinical data will be provided.

In summary, the hybrid mice established by the present invention have the following advantages in the study of hepatitis and hepatocellular carcinoma. (1) the hybrid mice of hepatitis B virus gene transgenic mice and miR-122 knock-out mice have a high concentration of hepatitis B virus DNA and down-regulated miR-122, which is very similar to the condition of human hepatitis B virus infection, and have a very high (>90%) incidence of spontaneous hepatocellular carcinoma. The pathological characteristics of mouse hepatocellular carcinoma are similar to human hepatocellular carcinoma, which can be used as an ideal animal model for hepatitis B virus-related hepatocellular carcinoma. Because of a very high (>90%) incidence of spontaneous hepatocellular carcinoma of the hybrid mice, a smaller number of the hybrid mice are needed for treatment groups and control groups for studies of experimental prevention or treatment of hepatocellular carcinoma to observe the efficacy, which is more cost-effective. (2) When the hybrid hepatitis B virus transgenic mice are five months old, the shape of the mitochondria in the liver tissue changes, and miR-122 is down-regulated, which is very suitable for studying effects of mitochondria dysfunction and down-regulation of miR-122 on fat metabolism and for development of novel therapeutic strategies. (3) Since the cancerous tissues of the hybrid mice have abnormal fat metabolism, reduced β-oxidation, and reduced vitamin A and retinoic acid in the cancerous tissues, the hybrid mice provide a research tool for correction of abnormal fat metabolism and supplementation of vitamin A and retinoic acid as a novel method for hepatocellular carcinoma prevention. (4) Research and development platform for hepatitis biomarkers. (5) Ideal research platform for screening novel drugs against hepatitis B virus and hepatoma.

Those of ordinary skill in the art will understand that changes may be made to the specific embodiments described above without departing from the broad inventive concept thereof. Therefore, it should be understood that the present invention is not limited to the specific embodiments disclosed, but is intended to cover modifications within the spirit and scope of the invention as defined by the scope of the appended claims.

What is claimed is:

1. A method for producing a transgenic animal model of mouse or rat for hepatocellular carcinoma, comprising:
   a) providing a polynucleotide expression vector encoding a hepatitis B virus (HBV) genome comprising enhancer I/II, open reading frames X, C, PS, and S at the 5' end and a polyadenylation site at the 3' end;
   b) introducing the polynucleotide expression vector into a genetic locus of a genome of an animal to produce a transgenic animal containing a genome encoding the HBV genome;
   c) providing an endogenous miR-122 knockout animal, which is the same species as the transgenic animal of step b); and
   d) hybridizing the transgenic animal containing the genome encoding the HBV genome and the endogenous miR-122 knockout animal to produce a transgenic animal having a genome encoding the HBV genome and the endogenous miR-122 knockout.

2. The method according to claim 1, wherein the HBV genome comprises genotype A, genotype B, genotype C, genotype D, genotype E, genotype F, genotype G, genotype H, genotype I, or genotype J.

3. The method according to claim 2, wherein the HBV genome is genotype B.

4. The method according to claim 1, wherein the HBV genome is a drug-resistant HBV genome.

5. The method according to claim 4, wherein the drug-resistant HBV genome is resistant to an antiviral nucleoside analogue.

6. The method according to claim 4, wherein the drug-resistant HBV genome is resistant to adefovir or lamivudine.

7. The method according to claim 4, wherein the drug-resistant HBV genome has at least one amino acid mutation selected from the group consisting of rtA181V, rtN236T, rtL180M, and rtM204V and a combination thereof in a reverse transcriptase region of the HBV genome, the numbers represent sites of the amino acid mutation, and the subsequent English letters are amino acids of the mutation.

8. The method according to claim 7, wherein the amino acid mutation is selected from the group consisting of rtL180M, rtM204V, and a combination thereof.

9. The method according to claim 1, wherein the endogenous miR-122 is single knocked out or double knocked out.

10. The method according to claim 1, wherein the endogenous miR-122 is single knocked out.

* * * * *

SEQUENCE LISTING

<160> NUMBER OF SEQ ID NOS: 5

<210> SEQ ID NO 1
<211> LENGTH: 3215
<212> TYPE: DNA
<213> ORGANISM: Hepatitis B virus

<400> SEQUENCE: 1

| | | | | | |
|---|---|---|---|---|---|
| ctccacaaca | ttccaccaag | ctctgctaga | tcccagagtg | agggggcctgt | atcttcctgc | 60 |
| tggtggctcc | agttccggaa | cagtaaaccc | tgttccgact | actgcctctc | ccacatcgtc | 120 |
| aatcttcttg | aggactgggg | accctgcacc | gaacatggag | aacacaacat | caggattcct | 180 |
| aggacccctg | ctcgtgttac | aggcggggtt | tttcttgttg | acaagaatcc | tcacaatacc | 240 |
| acagagtcta | gactcgtggt | ggacttctct | caattttcta | gggggagcac | ccgcgtgtcc | 300 |
| tggccaaaat | tcgcagtccc | caacctccaa | tcactcacca | acctcttgtc | ctccaatttg | 360 |
| tcctggctat | cgtggatgt | gtctgcggcg | ctttatcata | ttcctcttca | tcctgttgct | 420 |
| atgcctcatc | ttcttgttgg | ttcttctgga | ctatcaaggt | atgttgcccg | tttgtcctct | 480 |
| acttccagga | acatcaacaa | ccagtacggg | accatgcaag | acctgcacga | ctcctgctca | 540 |
| aggaacctct | atgcttccct | cttgttgctg | tacaaaacct | tcggacggaa | attgcacttg | 600 |
| tattcccatc | ccatcatctt | gggctttcgc | aagattccta | tgggagtggg | cctcagtccg | 660 |
| tttctcctgg | ttcagtttac | tagtgccatt | tgttcagtgg | ttcgtagggc | tttcccccac | 720 |
| tgtttggctt | tcagttatat | ggatgatgtg | gtattggggg | ccaagtctgt | acaacatctt | 780 |
| gagtcccttt | ttaccgctat | taccaatttt | cttttgtctt | tgggtataca | tttgaccct | 840 |
| aataaaacca | aacgttgggg | ctactccctt | aattttatgg | gatatgtaat | gggagttgg | 900 |
| ggtactttac | cacaggaaca | cattgtacta | aaactcaaac | aatgttttag | aaatcttcct | 960 |
| gtaaatagac | ctattgattg | gaaagtctgt | cagggaattg | tgggtctttt | gggctttgct | 1020 |
| gccccttta | cacaatgtgg | ctatcctgcc | ttaatgcctt | tgtatgcatg | tatacaagct | 1080 |
| aagcaggctt | tcactttctc | gccaacttac | aaggcttttc | tgtgtaaaca | atatctgaac | 1140 |
| ctttaccccg | ttgcccggca | acggtcaggt | ctctgccaag | tgtttgctga | cgcaaccccc | 1200 |
| actggatggg | gcttggccat | aggccatcag | cgcatgcgtg | gaacctttgt | ggctcctctg | 1260 |
| cccatccata | ctgcggaact | cctagccgct | tgttttgctc | gcagccggtc | tggggcaaaa | 1320 |
| ctcatcggaa | ccgacaactc | tgttgtcctc | tctcggaaat | acacctcctt | tccatggctg | 1380 |
| ctaggatgtg | ctgccaactg | gatcctgcgc | gggacgtcct | ttgtctacgt | cccgtcggcg | 1440 |
| ctgaatcccg | cggacgaccc | gtctcgcggc | cgtttgggcc | tctatcgtcc | ccttctacgt | 1500 |
| ctgccgttcc | ggccgaccac | ggggcgcacc | tctctttacg | cggtctcccc | gtctgtgcct | 1560 |
| tctcatctgc | cggaccgtgt | gcacttcgct | tcacctctgc | acgtcgcatg | gcgaccaccg | 1620 |
| tgaacgccca | ccaggtcttg | cccaaggtct | tacataagcg | gattcttgga | ctctcagcaa | 1680 |
| tgtcaacgac | cgaccttgag | gcgtacttca | aagactgttt | gtttaaagac | tgggaggagt | 1740 |
| tggggggagga | gattaggtta | atgatctttg | tactaggagg | ctgtaggcat | aaattggtct | 1800 |
| gttcaccagc | accatgcaac | ttttcacct | ctgcctaatc | atctcatgtt | catgtcctac | 1860 |
| tgttcaagcc | tccaagctgt | gccttgggtg | gctttgggc | atggacattg | acccgtataa | 1920 |
| agaacttgga | gcttctgtgg | agttactctc | tttttgcct | tcggacttct | ttccttctat | 1980 |
| tcgagatctc | ctcgacaccg | cctctgctct | gtatcgggag | gccttagagt | ctccggaaca | 2040 |
| ttgttcacct | caccatacag | cactcaggca | agctattctg | tgttggggtg | agttgatgaa | 2100 |

```
tctggccacc tgggtgggaa gtaatttgga agacccagca tccagggaat tagtagtcgg    2160
ctatgtcaat gttaatatgg gcctaaaact cagacaacta ttgtggtttc acatttcctg    2220
tcttactttt ggaagagaaa ctgtccttga gtatttggtg tcttttggag tgtggattcg    2280
cactcctacc gcttacagac caccaaatgc ccctatctta tcaacacttc cggaaactac    2340
tgttgttaga cgacgaggca ggtcccctag aagaagaact ccctcgcctc gcagacgaag    2400
gtctcaatcg ccgcgtcgca gaagatctca atctcgggaa tcccaatgtt agtatccctt    2460
ggactcataa ggtgggaaac tttactggac tttattcttc tactatacct gtctttaatc    2520
ctgagtggca aactccctcc tttcctcaca ttcatttgca ggaggacatt atcaatagat    2580
gtcaacaata tgtaggccct cttacagtta atgaaaaaag gagattaaaa ttaattatgc    2640
ctgccaggtt ctatcctaac cttaccaaat atttgcccct tagacaaaggc ataaaacctt    2700 actatccgga acatgcagtt aatcattact tcaaaactag gcattattta catactctgt    2760
ggaaggctgg tattctatat aagagagaaa ctacacgcag cgcctcattt tgtgggtcac    2820
catattcttg gaacaagag ctacagcatg ggaggtcagt attccacacc tcgaaaaggc    2880
atggggacga atctttctgt tcccaatcct ctgggattct ttcccgatca ccagttggac    2940
ccggcgttcg gagccaactc aaacaatcca gattgggact caaccccaa caaggatcaa    3000 tggccagagg caaatcaggt aggagtggga gcattcgggc cagggtcac cccaccacac    3060 ggtggtcttt tggggtggag ccctcaggcg caggcatac tgacaacagt gccagcagcg    3120
cctcctcctg ctaccaccaa tcggcagtca ggaagacagc ctactcccat ctctccacct    3180
ctcagagaca gtcatcctca ggccatacag tggaa                              3215

<210> SEQ ID NO 2
<211> LENGTH: 3215
<212> TYPE: DNA
<213> ORGANISM: Hepatitis B virus

<400> SEQUENCE: 2
ctccaccact ttccacaaaa ctcttcaaga tcccagagtc agggccctgt acattcctgc     60
tggtggctcc agttcaggaa cagtgagccc tgctcagagt actgtctcgg ccatatcgtc    120
aatcttatcg aagactgggg accctgtact gaacatggag aacatcgcat caggactcct    180
aggacccctg ctcgtgttac aggcggggtt tttcttgttg acaaaaatcc tcacaatacc    240
acagagtcta gactcgtggt ggacttctct caattttcta ggggacacac ccgtgtgtct    300
tggccaaaat tcgcagtccc aaatctccag tcactcacca acctgttgtc ctccaatttg    360
tcctggttat cgctggatgt gtctgcggcg ttttatcatc ttcctctgca tcctgctgct    420
atgcctcatc ttcttgttgg ttcttctgga ctatcaaggt atgttgcccg tttgtcctct    480
aattccagga tcatcaacaa ccagcaccgg accatgcaaa acctgcacga ctcctgctca    540
aggaacctct atgtttccct catgttgctg tacaaaacct acggacggaa actgcacctg    600
tattcccatc ccatcatctt gggctttcgc aaaattccta tgggagtggg cctcagtccg    660
tttctcatgg ctcagtttac tagtgccatt tgttcagtgg ttcgtagggc ttttccccac    720
tgtctggctt tcagttatgt ggatgatgtg gtattggggg ccaagtctgt acaacatctt    780
gagtcccttt ctgccgctgt taccaatttt cttttgtctt tgggtataca tttaaaccct    840
cacaaaacaa aagatggggg atattccctt aacttcatgg gatatgtaat tgggagttgg    900
ggcacattgc cacaggaaca tattgtacaa aaaatcaaaa tgtgtttag aaaactccct    960
```

-continued

```
gtaaacaggc ctattgattg gaaagtatgt caacgaattg tgggtctttt ggggtttgcc      1020
gctcctttca cgcaatgtgg atatcctgcc ttaatgcctt tatatgcatg tatacaagca      1080
aaacaggctt ttacttttc gccaacttac aaggcctttc taagtaaaca gtatctgaac       1140
ctttaccccg ttgctcggca acggcctggt ctgtgccaag tgtttgctga cgcaaccccc      1200
actggttggg gcttggccat aggccatcag cgcatgcgtg gaacctttgt gtctcctctg      1260
ccgatccata ctgcggaact cctagccgct tgttttgctc gcagcaggtc tggggcaaaa      1320
ctcatcggga ctgacaattc tgtcgtgctc tcccgcaagt atacatcatt ccatggctg       1380
ctaggctgtg ctgccaactg gatcctgcgc gggacgtcct ttgtttacgt cccgtcggcg      1440
ctgaatcccg cggacgaccc ctcccggggc cgcttgggc tctaccgccc gcttctccgc       1500
ctttggtacc gaccgaccac ggggcgcacc tctctttacg cggactcccc gtctgtgcct      1560
tctcatctgc cggaccgtgt gcacttcgct tcacctctgc acgtcgcatg gagaccaccg      1620
tgaacgccca caggaacctg cccaaggtct tgcataagag gactcttgga ctttcagcaa      1680
tgtcaacgac cgaccttgag gcatacttca aagactgtgt gtttaatgag tgggaggagt      1740
tgggggagga ggttaggtta atgatctttg tactaggagg ctgtaggcat aaattggtgt      1800
gttcaccagc accatgcaac ttttttcacct ctgcctaatc atctcatgtt catgtcctac     1860
tgttcaagcc tccaagctgt gccttgggtg gctttggggc atggacattg acccgtataa      1920
agaatttgga gcttctgtgg agttactctc tttttgcct tctgactttt ttccttctat       1980
tcgagatctc ctcgacaccg cctctgcttt gtatcgggag gccttagagt ctccggaaca      2040
ttgttcacct caccatacgg cactcaggca agctattctg tgttggggtg agttaatgaa      2100
tctagccacc tgggtgggaa gtaatttgga agatccagca tccagggaat tagtagtcag      2160
ctatgtcaac gttaatatgg gcctaaaaat cagacaacta ttgtggtttc acatttcctg     2220
tcttactttt gggagagaaa ctgttcttga atatttggtg tcttttggag tgtggattcg      2280
cactcctcct gcatatagac caccaaatgc ccctatctta tcaacacttc cggaaactac      2340
tgttgttaga cgaagaggca ggtcccctag aagaagaact ccctcgcctc gcagacgaag      2400
gtctcaatcg ccgcgtcgca gaagatctca atctcgggaa tctcaatgtt agtattcctt      2460
ggacacataa ggtgggaaac tttacggggc tttattcttc tacggtacct tgctttaatc      2520
ctaactggca aactccttct tttcctgaca ttcatttgca ggaggacatt gttgatagat      2580
gtaagcaatt tgtggggccc cttacagtaa atgaaaacag gagactaaaa ttaattatgc      2640
ctgctaggtt ttatcccaat gttactaaat atttgccctt agataaaggg atcaaaccgt      2700
attatccaga gtatgtagtt aatcattact tccagacgcg acattattta catactctt       2760
ggaaggcggg gatcttatat aaaagagagt ccacacgtag cgcctcattt tgcgggtcac      2820
catattcttg ggaacaagat ctacagcatg ggaggttggt cttccaaacc tcgaaaaggc     2880
atggggacaa atctttctgt ccccaatccc ctgggattct tccccgatca tcagttggac     2940
cctgcattca aagccaactc aaaaaatcca gattgggacc tcaacccgcg caaggacaac     3000
tggccggacg ccaacaaggt gggagtggga gcattcgggc cagggttcac ccctccccgt     3060
gggggactgt tggggtggag ccctcaggct cagggccaac tcacaactgt gccagcggct     3120
cctcctcctg cctccaccaa tcggcagtca ggaaggcagc ctactcccct atctccacct     3180
ctaagggaca ctcatcctca ggccatgcag tggaa                                3215
```

<210> SEQ ID NO 3
<211> LENGTH: 3214

```
<212> TYPE: DNA
<213> ORGANISM: Hepatitis B virus

<400> SEQUENCE: 3
ctccacaaca ttccaccaag ctctgctaga tcccagagtg aggggcctgt atcttcctgc      60
tggtggctcc agttccggaa cagtaaaccc tgttccgact actgcctctc ccacatcgtc     120
aatcttcttg aggactgggg accctgcacc gaacatggag aacacaacat caggattcct     180
aggaccctg ctcgtgttac aggcggggtt tttcttgttg acaagaatcc tcacaatacc     240
acagagtcta gactcgtggt ggacttctct caattttcta gggggaacac ccaggtgtcc     300
tggccaaaat tcgcagtccc caacctccaa tcactcacca acctcttgtc ctccaatttg     360
tcctggctat cgttggatgt gtctgcggcg ttttatcata ttcctcttca tcctgctgct     420
atgcctcatc ttcttgttgg ttcttctgga ctatcaaggt atgttgcccg tttgtcctct     480
acttccagga acatcaacaa ccagcacggg accatgcaag acctgcacga ctcctgctca     540
aggaacctct atgtttccct cttgttgctg tacaaaacct tcggacggaa attgcacttg     600
tattcccatc ccatcatctt gggctttcgc aagataccta tgggagtggg cctcagtccg     660
tttctcttgg ctcagtttac tagtgccatt tgttcagtgg ttcgtagggc tttcccccac     720
tgtttggctt tcagttatat ggatgatgtg gtattggggg ccaagtctgt acaacatctt     780
gagtcccttt ttaccgctat tactaatttt ctgttgtctt gggtataca tttaaaccct     840
aataaaacca aacgttgggg ctactccctt aattttatgg gatatgtaat gggagttgg     900
ggtactttac cacaggaaca cattgtacta aaactcaaac aatgttttag aaaacttcct     960
gtaaatagac ctattgattg gaaagtatgt cagagaattg tgggtctttt gggctttgct    1020
gccccttttta cacaatgtgg ctatcctgcc ttaatgcctt tgtatgcatg tatacaagct    1080
aagcaggctt ttacttttctc gccaacttat aaggcttttc tgtgtcaaca atatctgaac    1140
ctctaccccg ttgcccggca acggtctggt ctctgccaag tgtttgctga cgcaaccccc    1200
actggctggg gcttggccat aggccatcag cgcatgcgtg gaacctttgt ggctcctctg    1260
ccgatccata ctgcagaact cctagccgct tgttttgctc gcagccggtc tggggcgaaa    1320
ctcatcggaa ccgacaactc tgttgtcctc tctcggaagt acacctcctt tccatggctg    1380
ctaggatgtg ctgccagctg gatcctgcgc gggacgtcct ttgtctacgt cccgtcggcg    1440
ctgaatcccg cggacgaccc gtctcgcggc cgtttgggcc tctatcgtcc ccttctacgt    1500
ctgccgttcc ggccgaccac ggggcgcacc tctctttacg cggtctcccc gtctgtgcct    1560
tctcatctgc cggaccgtgt gcacttcgct tcacctctgc acgtcgcatg gcgaccaccg    1620
tgaacgccca ccaggtcttg cccaaggtct tacataagcg gattcttgga ctctcagcaa    1680
tgtcaacgac cgaccttgag gcgtacttca aagactgttt gtttaaagac tgggaggagt    1740
tggggagga gattaggtta atgatctttg tactaggagg ctgtaggcat aaattggtct    1800
gttcaccagc accatgcaac ttttccacct ctgcctaatc atctcatgtt catgtcctac    1860
tgttcaagcc tccaagctgt gccttgggtg gctttgggc atggacattg acccgtataa    1920
agaacttgga gcttctgtgg agttactctc tttttgcct tcggacttct ttccttctat    1980
tcgagatctc ctcgacaccg cctctgctct gtatcgggag gccttagagt ctccggaaca    2040
ttgttcacct caccatacag cactcaggca agctattctg tgttgggtg agttgatgaa    2100
tctggccacc tgggtgggaa gtaatttgga agacccagca tccagggaat tagtagtcgg    2160
ctatgtcaat gttaatatgg gcctaaaact cagacaacta ttgtggtttc acatttcctg    2220
```

| | |
|---|---:|
| tcttactttt ggaagagaaa ctgtccttga gtatttggtg tcttttggag tgtggattcg | 2280 |
| cactcctacc gcttacagac caccaaatgc ccctatctta tcaacacttc cggaaactac | 2340 |
| tgttgttaga cgacgaggca ggtcccctag aagaagaact ccctcgcctc gcagacgaag | 2400 |
| gtctcaatcg ccgcgtcgca gaagatctca atctcgggaa tcccaatgtt agtatccctt | 2460 |
| ggactcataa ggtgggaaac tttactggac tttattcttc tactatacct gtctttaatc | 2520 |
| ctgagtggca aactccctcc tttcctcaca ttcatttgca ggaggacatt atcaatagat | 2580 |
| gtcaacaata tgtaggccct cttacagtta atgaaaaaag gagattaaaa ttaattatgc | 2640 |
| ctgccaggtt ctatcctaac cttaccaaat atttgccctt agacaaaggc ataaaacctt | 2700 |
| actatccgga acatgcagtt aatcattact tcaaaactag gcattattta catactctgt | 2760 |
| ggaaggctgg tattctatat aagagagaaa ctacacgcag cgcctcattt tgtgggtcac | 2820 |
| catattcttg ggaacaagag ctacagcatg ggaggtcagt attccacacc tcgaaaaggc | 2880 |
| atggggacga atctttctgt tcccaatcct ctgggattct ttcccgatca ccagttggac | 2940 |
| ccggcgttcg gagccaactc aaacaatcca gattgggact tcaaccccaa caaggatcaa | 3000 |
| tggccagagg caaatcaggt aggagtggga gcattcgggc cagggtcac cccaccacac | 3060 |
| ggtggtctt tggggtggag ccctcaggcg cagggcatac tgcaacagt gccagcagcg | 3120 |
| cctcctcctg ctaccaccaa tcggcagtca ggaagacagc ctactcccat ctctccacct | 3180 |
| ctcagagaca gtcatcctca ggccatacag tgga | 3214 |

<210> SEQ ID NO 4
<211> LENGTH: 4765
<212> TYPE: DNA
<213> ORGANISM: Hepatitis B virus

<400> SEQUENCE: 4

| | |
|---|---:|
| gtcgactggg tcttttgggg tttgccgctc ctttcacgca atgtggatat cctgccttaa | 60 |
| tgcctttata tgcatgtata caagcaaaac aggcttttac ttttcgcca acttacaagg | 120 |
| cctttctaag taaacagtat ctgaaccttt accccgttgc tcggcaacgg cctggtctgt | 180 |
| gccaagtgtt tgctgacgca accccactg gttggggctt ggccataggc catcagcgca | 240 |
| tgcgtggaac ctttgtgtct cctctgccga tccatactgc ggaactccta gccgcttgtt | 300 |
| ttgctcgcag caggtctggg gcaaaactca tcgggactga caattctgtc gtgctctccc | 360 |
| gcaagtatac atcatttcca tggctgctag gctgtgctgc caactggatc ctgcgcggga | 420 |
| cgtcctttgt ttacgtcccg tcggcgctga atcccgcgga cgaccctcc cggggccgct | 480 |
| tggggctcta ccgcccgctt ctccgccttt ggtaccgacc gaccacgggg cgcacctctc | 540 |
| tttacgcgga ctccccgtct gtgccttctc atctgccgga ccgtgtgcac ttcgcttcac | 600 |
| ctctgcacgt cgcatggaga ccaccgtgaa cgcccacagg aacctgccca aggtcttgca | 660 |
| taagaggact cttggacttt cagcaatgtc aacgaccgac cttgaggcat acttcaaaga | 720 |
| ctgtgtgttt aatgagtggg aggagttggg ggaggaggtt aggttaatga tctttgtact | 780 |
| aggaggctgt aggcataaat tggtgtgttc accagcacca tgcaacttttt tcacctctgc | 840 |
| ctaatcatct catgttcatg tcctactgtt caagcctcca agctgtgcct tgggtggctt | 900 |
| tggggcatgg acattgaccc gtataaagaa tttggagctt ctgtggagtt actctctttt | 960 |
| ttgccttctg acttttttcc ttctattcga gatctcctcg acaccgcctc tgctttgtat | 1020 |
| cgggaggcct tagagtctcc ggaacattgt tcacctcacc atacggcact caggcaagct | 1080 |
| attctgtgtt ggggtgagtt aatgaatcta gccacctggg tgggaagtaa tttggaagat | 1140 |

```
ccagcatcca gggaattagt agtcagctat gtcaacgtta atatgggcct aaaaatcaga    1200
caactattgt ggtttcacat ttcctgtctt acttttggga gagaaactgt tcttgaatat    1260
ttggtgtctt ttggagtgtg gattcgcact cctcctgcat atagaccacc aaatgcccct    1320
atcttatcaa cacttccgga aactactgtt gttagacgaa gaggcaggtc ccctagaaga    1380
agaactccct cgcctcgcag acgaaggtct caatcgccgc gtcgcagaag atctcaatct    1440
cgggaatctc aatgttagta ttccttggac acataaggtg ggaaacttta cggggcttta    1500
ttcttctacg gtaccttgct ttaatcctaa ctggcaaact ccttcttttc ctgacattca    1560
tttgcaggag acattgttg atagatgtaa gcaatttgtg ggcccctta cagtaaatga     1620 aaacaggaga ctaaaattaa ttatgcctgc taggttttat cccaatgtta ctaaatattt    1680
gcccttagat aaagggatca aaccgtatta tccagagtat gtagttaatc attacttcca    1740
gacgcgacat tatttacata ctctttggaa ggcggggatc ttatataaaa gagagtccac    1800
acgtagcgcc tcattttgcg ggtcaccata ttcttgggaa caagatctac agcatgggag    1860
gttggtcttc caaacctcga aaaggcatgg ggacaaatct ttctgtcccc aatccctgg     1920 gattcttccc cgatcatcag ttggaccctg cattcaaagc caactcaaaa atccagatt     1980 gggacctcaa cccgcgcaag acaactggc cggacgccaa caaggtggga gtgggagcat     2040
tcgggccagg gttcacccct ccccgtgggg gactgttggg gtggagccct caggctcagg    2100
gccaactcac aactgtgcca gcggctcctc ctcctgcctc caccaatcgg cagtcaggaa    2160
ggcagcctac tccctatct ccacctctaa gggacactca tcctcaggcc atgcagtgga     2220
actccaccac tttccacaaa actcttcaag atcccagagt cagggccctg tacattcctg    2280
ctggtggctc cagttcagga acagtgagcc ctgctcagag tactgtctcg gccatatcgt    2340
caatcttatc gaagactggg gaccctgtac tgaacatgga gaacatcgca tcaggactcc    2400
taggacccct gctcgtgtta caggcgggggt ttttcttgtt gacaaaaatc ctcacaatac    2460
cacagagtct agactcgtgg tggacttctc tcaattttct aggggggcaca cccgtgtgtc    2520 ttggccaaaa ttcgcagtcc caaatctcca gtcactcacc aacctgttgt cctccaattt    2580
gtcctggtta tcgctggatg tgtctgcggc gttttatcat cttcctctgc atcctgctgc    2640
tatgcctcat cttcttgttg gttcttctgg actatcaagg tatgttgccc gtttgtcctc    2700
taattccagg atcatcaaca accagcaccg gaccatgcaa aacctgcacg actcctgctc    2760
aaggaacctc tatgtttccc tcatgttgct gtacaaaacc tacggacgga aactgcacct    2820
gtattcccat cccatcatct tgggcttcg caaaattcct atgggagtgg gcctcagtcc     2880
gtttctcttg gctcagtttta ctagtgccat tgttcagtg gttcgtaggg ctttcccca     2940 ctgtctggct ttcagttata tggatgatgt ggttttgggg gccaagtctg tacaacatct    3000
tgagtccctt tatgccgctg ttaccaattt tcttttgtct ttgggtatac atttaaaccc    3060
tcacaaaaca aaaagatggg gatattccct taacttcatg gatatgtaa ttgggagttg     3120 gggcacattg ccacaggaac atattgtaca aaaaatcaaa atgtgtttta gaaaactccc    3180
tgtaaacagg cctattgatt ggaaagtatg tcaacgaatt gtgggtcttt tggggtttgc    3240
cgctcctttc acgcaatgtg gatatcctgc cttaatgcct ttatatgcat gtatacaagc    3300
aaaacaggct tttacttttt cgccaactta caaggccttt ctaagtaaac agtatctgaa    3360
cctttacccc gttgctcggc aacggcctgg tctgtgccaa gtgtttgctg acgcaacccc    3420
cactggttgg ggcttggcca taggccatca gcgcatgcgt ggaacctttg tgtctcctct    3480
```

| | |
|---|---|
| gccgatccat actgcggaac tcctagccgc ttgttttgct cgcagcaggt ctggggcaaa | 3540 |
| actcatcggg actgacaatt ctgtcgtgct ctcccgcaag tatacatcat ttccatggct | 3600 |
| gctaggctgt gctgccaact ggatcctgcg cgggacgtcc tttgtttacg tcccgtcggc | 3660 |
| gctgaatccc gcggacgacc cctcccgggg ccgcttgggg ctctaccgcc cgcttctccg | 3720 |
| cctttggtac cgaccgacca cggggcgcac ctctctttac gcggactccc cgtctgtgcc | 3780 |
| ttctcatctg ccgaccgtg tgcacttcgc ttcacctctg cacgtcgcat ggagaccacc | 3840 |
| gtgaacgccc acaggaacct gcccaaggtc ttgcataaga ggactcttgg actttcagca | 3900 |
| atgtcaacga ccgaccttga ggcatacttc aaagactgtg tgtttaatga gtgggaggag | 3960 |
| ttgggggagg aggttaggtt aatgatcttt gtactaggag gctgtaggca taaattggtg | 4020 |
| tgttcaccag caccatgcaa cttttttcacc tctgcctaat catctcatgt tcatgtccta | 4080 |
| ctgttcaagc ctccaagctg tgccttgggt ggctttgggg catggacatt gacccgtata | 4140 |
| aagaatttgg agcttctgtg gagttactct ctttttttgcc ttctgactt tttccttcta | 4200 |
| ttcgagatct cctcgacacc gcctctgctt tgtatcggga ggcttagag tctccggaac | 4260 |
| attgttcacc tcaccatacg gcactcaggc aagctattct gtgttggggt gagttaatga | 4320 |
| atctagccac ctgggtggga agtaatttgg aagatccagc atccagggaa ttagtagtca | 4380 |
| gctatgtcaa cgttaatatg ggcctaaaaa tcagacaact attgtggttt cacatttcct | 4440 |
| gtcttacttt tgggagagaa actgttcttg aatatttggt gtcttttgga gtgtggattc | 4500 |
| gcactcctcc tgcatataga ccaccaaatg cccctatctt atcaacactt ccggaaacta | 4560 |
| ctgttgttag acgaagaggc aggtcccta gaagaagaac tccctcgcct cgcagacgaa | 4620 |
| ggtctcaatc gccgcgtcgc agaagatctc aatctcggga atctcaatgt tagtattcct | 4680 |
| tggactcata aggtgggata tcactagtga attccaccac actggactag tggatccgag | 4740 |
| ctcggtacca agcttaagtt taaac | 4765 |

<210> SEQ ID NO 5
<211> LENGTH: 1211
<212> TYPE: DNA
<213> ORGANISM: Artificial Sequence
<220> FEATURE:
<223> OTHER INFORMATION: HS4 insulator DNA

<400> SEQUENCE: 5

| | |
|---|---|
| gagctcacgg ggacagcccc cccccaaagc ccccagggat gtaattacgt ccctcccccg | 60 |
| ctaggggca gcagcgagcc gcccgggggct ccgctccggt ccggcgctcc ccccgcatcc | 120 |
| ccgagccggc agcgtgcggg gacagcccgg gcacggggaa ggtggcacgg gatcgctttc | 180 |
| ctctgaacgc ttctcgctgc tctttgagcc tgcagacacc tgggggata cggggaaaaa | 240 |
| gctttaggct gaaagagaga tttagaatga cagaatcata gaacggcctg ggttgcaaag | 300 |
| gagcacagtg ctcatccaga tccaaccccc tgctatgtgc agggtcatca accagcagcc | 360 |
| caggctgccc agagccacat ccagcctggc cttgaatgcc tgcagggatg gggcatccac | 420 |
| agcctccttg ggcaacctgt tcagtgcgtc accaccctct gggggaaaaa ctgcctcctc | 480 |
| atatccaacc caaacctccc ctgtctcagt gtaaagccat tccccttgt cctatcaagg | 540 |
| gggagtttgc tgtgacattg ttggtctggg gtgacacatg tttgccaatt cagtgcatca | 600 |
| cggagaggca gatctggggg ataaggaagt gcaggacagc atggacgtgg gacatgcagg | 660 |
| tgttgagggc tctgggacac tctccaagtc acagcgttca gaacagcctt aaggataaga | 720 |
| agataggata gaaggacaaa gagcaagtta aaacccagca tggagaggag cacaaaaagg | 780 |

```
ccacagacac tgctggtccc tgtgtctgag cctgcatgtt tgatggtgtc tggatgcaag      840 cagaagggggt ggaagagctt gcctggagag atacagctgg gtcagtagga ctgggacagg      900
cagctggaga attgccatgt agatgttcat acaatcgtca aatcatgaag gctggaaaag      960
ccctccaaga tccccaagac caaccccaac ccacccaccg tgcccactgg ccatgtccct     1020
cagtgccaca tccccacagt tcttcatcac ctccagggac ggtgacccccc ccacctccgt     1080 gggcagctgt gccactgcag caccgctctt tggagaaggt aaatcttgct aaatccagcc     1140
cgaccctccc ctggcacaac gtaaggccat tatctctcat ccaactccag gacggagtca     1200
gtgagaatat t                                                           1211
```